(12) United States Patent
Pop et al.

(10) Patent No.: US 8,714,246 B2
(45) Date of Patent: May 6, 2014

(54) DOWNHOLE MEASUREMENT OF FORMATION CHARACTERISTICS WHILE DRILLING

(75) Inventors: Julian J. Pop, Houston, TX (US); Reza Taherian, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 679 days.

(21) Appl. No.: 12/993,275

(22) PCT Filed: Apr. 27, 2009

(86) PCT No.: PCT/US2009/041784
§ 371 (c)(1),
(2), (4) Date: Nov. 18, 2010

(87) PCT Pub. No.: WO2009/142873
PCT Pub. Date: Nov. 26, 2009

(65) Prior Publication Data
US 2011/0088895 A1 Apr. 21, 2011

Related U.S. Application Data

(60) Provisional application No. 61/055,201, filed on May 22, 2008.

(51) Int. Cl.
*E21B 47/00* (2012.01)

(52) U.S. Cl.
USPC ........ 166/264; 175/59; 73/152.24; 73/152.04

(58) Field of Classification Search
USPC ............. 166/264; 175/59; 73/152.24–152.26, 73/152.19, 152.04
See application file for complete search history.

(56) References Cited

U.S. PATENT DOCUMENTS

| | | |
|---|---|---|
| 4,635,735 A | 1/1987 | Crownover |
| 4,833,915 A | 5/1989 | Radd et al. |
| 5,113,953 A | 5/1992 | Noble |
| 5,265,682 A | 11/1993 | Russell et al. |
| 5,520,255 A | 5/1996 | Barr et al. |
| 5,553,678 A | 9/1996 | Barr et al. |
| 5,553,679 A | 9/1996 | Thorp |
| 5,582,259 A | 12/1996 | Barr |
| 5,603,385 A | 2/1997 | Colebrook |
| 5,673,763 A | 10/1997 | Thorp |
| 5,685,379 A | 11/1997 | Barr et al. |
| 5,695,015 A | 12/1997 | Barr et al. |
| 5,706,905 A | 1/1998 | Barr |
| 5,778,992 A | 7/1998 | Fuller |
| 5,803,185 A | 9/1998 | Barr et al. |
| 5,971,085 A | 10/1999 | Colebrook |
| 6,089,332 A | 7/2000 | Barr et al. |
| 6,092,610 A | 7/2000 | Kosmala et al. |
| 6,158,529 A | 12/2000 | Dorel |
| 6,176,323 B1 * | 1/2001 | Weirich et al. ................. 175/40 |
| 6,244,361 B1 | 6/2001 | Comeau et al. |
| 6,290,000 B1 | 9/2001 | Zamfes |
| 6,364,034 B1 | 4/2002 | Schoeffler |

(Continued)

*Primary Examiner* — Shane Bomar
*Assistant Examiner* — Kipp Wallace
(74) *Attorney, Agent, or Firm* — Cathy Hewitt; John Vereb

(57) ABSTRACT

Methods and apparatus for acquiring mud gas logging data, comparing the mud gas logging data to second data associated with a sidewall fluid sample measurement, and adjusting calibration data associated with a mud gas logging tool based on the comparison of the mud gas logging data and the second data associated with the sidewall fluid sample measurement.

17 Claims, 12 Drawing Sheets

(56) References Cited

U.S. PATENT DOCUMENTS

| | | |
|---|---|---|
| 6,394,193 B1 | 5/2002 | Askew |
| 6,401,842 B2 | 6/2002 | Webb et al. |
| 7,458,257 B2 | 12/2008 | Pop et al. |
| 2001/0052428 A1 | 12/2001 | Larronde et al. |
| 2002/0194907 A1* | 12/2002 | Bostrom et al. ............ 73/152.58 |
| 2005/0241382 A1* | 11/2005 | Coenen ...................... 73/152.19 |
| 2007/0029112 A1 | 2/2007 | Li et al. |
| 2007/0119244 A1 | 5/2007 | Goodwin et al. |
| 2007/0137293 A1* | 6/2007 | Pop et al. ................... 73/152.23 |
| 2008/0066537 A1* | 3/2008 | Hegeman et al. .......... 73/152.28 |

* cited by examiner

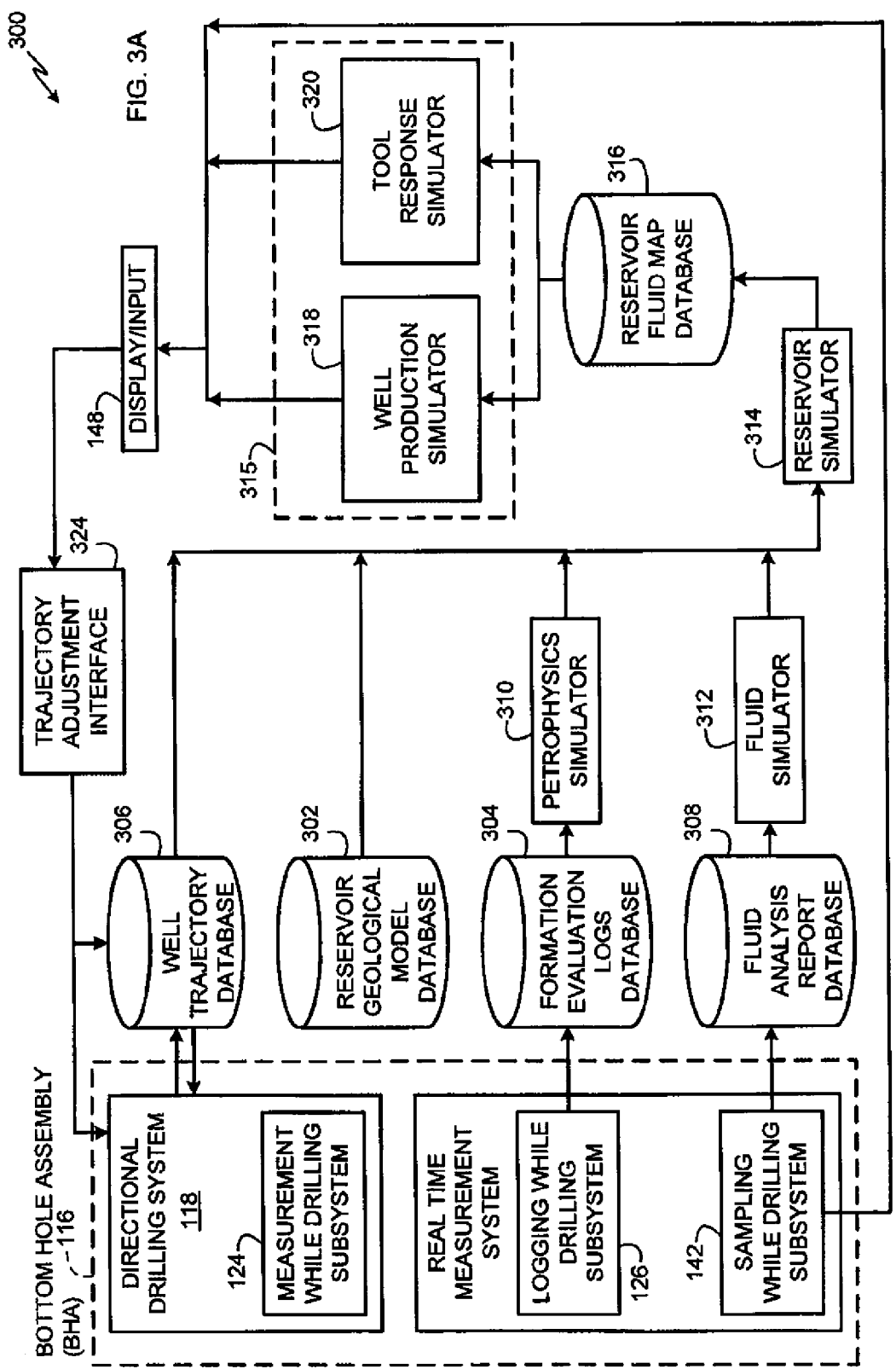

DOWNHOLE MEASUREMENT OF FORMATION CHARACTERISTICS WHILE DRILLING

BACKGROUND OF THE DISCLOSURE

Drilling, completion, and production of hydrocarbon reservoir wells involve drilling boreholes that intersect or traverse hydrocarbon-bearing deposits. Typically, drilling rigs at the surface are used to drill boreholes to reach the location of subsurface oil or gas deposits and establish fluid communication between the deposits and the surface via the borehole. Downhole drilling equipment may be directed or steered to the oil or gas deposits using directional drilling techniques.

Evaluations of subterranean formations penetrated by the borehole can be used to identify subsurface formations having characteristics indicative of good production and/or drainage. To perform such evaluations, the drilling equipment may be removed from the borehole and a wireline tool can be deployed into the borehole to sample and/or test one or more formation fluids at various stations or positions of the wireline tool. Alternatively, the drilling equipment of a drill string may include a downhole tool configured to sample and/or test the fluids of the surrounding subterranean formation. The sampling may be accomplished using formation testing tools that retrieve the formation fluids at desired borehole positions or stations and/or test the retrieved fluids in situ. Alternatively, formation fluids may be collected in one or more chambers of the downhole tool which are then brought to the surface and evaluated to determine the properties of the fluids and the condition of the subterranean formations, and thereby locate exploitable oil and/or gas deposits.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 3A depicts a block diagram of an example apparatus that may be used to analyze well data to control a drill string to form a well.

DETAILED DESCRIPTION

Figure 1A:
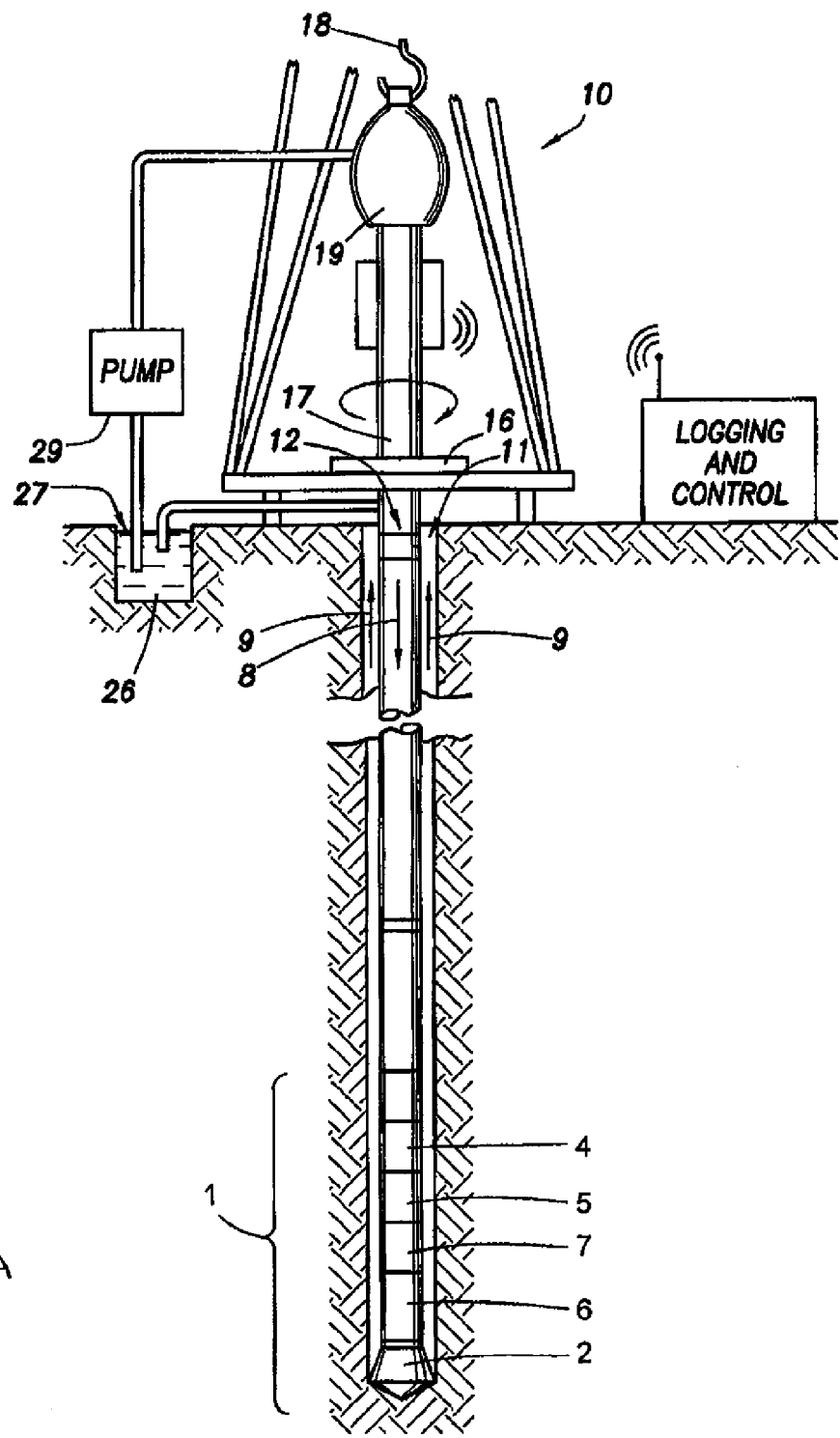
FIG. 1A is an elevation view of a wellsite system that may be used to implement the example methods and apparatus described herein.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

The example methods and apparatus described herein may be used to determine a well trajectory based on real-time or substantially real-time downhole measurements of reservoir fluid properties. The example methods and apparatus may be used during exploration and appraisal phases of a reservoir. For example, the example methods and apparatus may be used to steer a drill string to form the well trajectory so that useful information about the fluid distribution in the reservoir can be measured. Thus, in some example implementations, the well trajectory may be adjusted to optimize reservoir characterization.

The example methods and apparatus described herein may also be used during a development phase of a reservoir. For example, the example methods and apparatus may be used to steer a drill string so that a producing well engages hydrocarbon accumulations of sufficient economical value. Alternatively, the example methods and apparatus may be used to steer a drill string so that an injection well (e.g., a gas injection well) engages particular flow units in the reservoir. Thus, in some example implementations, the well trajectory may be adjusted to optimize the reservoir drainage/production, either directly (as in the case of a producing well) or indirectly (as in the case of an injection well).

The example methods and apparatus described herein may be implemented to use in-situ measurements indicative of formation fluid properties and/or a reservoir fluid property map. A formation fluid property may be determined by measuring a property of downhole fluid in or extracted from formation rock surrounding the borehole of a well. A reservoir extends beyond the immediate formation rock surrounding the borehole of a well. A reservoir fluid property map may be determined from the measured fluid property using various extrapolation techniques further detailed herein.

In some example implementations that use formation fluid properties to control a drill string to form a well trajectory, the example methods and apparatus described herein may be configured to determine a reservoir fluid property map on a portion of a reservoir; convey at least one fluid property sensor into a reservoir well using, for example, a drill string; perform in-situ measurements using the sensor indicative of a formation fluid property; compare the in-situ measurements with the property map; and adjust a well trajectory based on the comparison. In such example implementations, the example methods and apparatus may also be configured to determine a reservoir fluid property uncertainty map on at least the same portion of the reservoir; determine the uncertainty associated with the in-situ measurements performed by the sensor; and compare the in-situ measurement uncertainties with the property map and/or its associated uncertainty map.

In some example implementations that use reservoir fluid properties to control a drill string to form a well trajectory, the example methods and apparatus described herein may be configured to convey at least one fluid property sensor into a reservoir well using, for example, a drill string; perform at least one in-situ measurement using the sensor indicative of a reservoir fluid property; determine a reservoir fluid property map on a portion of the reservoir based on the in-situ measurement; and adjust a well trajectory based on the determined property map. In such example implementations, the example methods and apparatus may also be configured to determine a reservoir fluid property uncertainty map associated with the at least one measurement and adjust a well trajectory based on the property map and/or the uncertainty indicated by the property uncertainty map.

In the examples described herein, the formation and/or reservoir fluid properties may include properties that are related (e.g., first-order related) to the reservoir fluid composition. The fluid properties may be one or more (e.g., in combination) of fluid compositions (e.g., either a partial or a full description composition), constituent isotope ratios, gas-liquid ratios, etc. Fluid composition data may alternatively be described with thermo-physical data such as, for example, fluid bulk density, saturation pressures, viscosity, fluid acoustic impedance (i.e., the square root of the product of the fluid compressibility by the fluid density), and fluid compressibility at a given pressure and temperature. In addition, fluid composition data may also be represented by raw spectroscopic data such as, for example, a spectrum of mass fragments as used in mass spectrometry, a spectrum of optical densities, fluorescence data, refractive index data, nuclear magnetic resonance (NMR) data, and dielectric spectrum data. In some example implementations, fluid properties may additionally or alternatively be represented or described using parameters or sets of parameters used in equations that describe characteristics of a fluid such as, for example, sets of parameters used in equations of state (EoS) or coefficients used, for example, as part of neural network methods and/or radial basis functions which are fit to entries contained in one or more fluid property databases.

Although the example methods and apparatus described herein may be used to adjust a well trajectory by adjusting the direction, travel, and path of a well trajectory, adjusting a well trajectory as described herein may also include terminating all further planned drilling operations. Such may be the case where in-situ measurements indicate that it would not be productive to continue drilling a particular well in a particular reservoir or at a particular position in the reservoir.

FIG. 1A illustrates a wellsite system in which the example methods and apparatus described herein can be employed. The wellsite can be onshore or offshore. In this example system, a borehole 11 is formed in subsurface formations by rotary drilling in a manner that is well known. Example implementations of the example methods and apparatus can also use directional drilling, as will be described hereinafter.

A drill string 12 is suspended within the borehole 11 and has a bottom hole assembly 1 which includes a drill bit 2 at its lower end. The surface system includes platform and derrick assembly 10 positioned over the borehole 11, the assembly 10 including a rotary table 16, a kelly 17, a hook 18, and a rotary swivel 19. The drill string 12 is rotated by the rotary table 16, energized by means not shown, which engages the kelly 17 at the upper end of the drill string 12. The drill string 12 is suspended from the hook 18, attached to a traveling block (not shown), through the kelly 17 and the rotary swivel 19, which permits rotation of the drill string 12 relative to the hook 18. As is well known, a top drive system could alternatively be used.

In the illustrated example implementation, the surface system further includes drilling fluid or mud 26 stored in a pit 27 formed at the well site. A pump 29 delivers the drilling fluid 26 to the interior of the drill string 12 via a port in the swivel 19, causing the drilling fluid to flow downwardly through the drill string 12 as indicated by the directional arrow 8. The drilling fluid exits the drill string 12 via ports in the drill bit 2, and then circulates upwardly through the annulus region between the outside of the drill string 12 and the wall of the borehole, as indicated by the directional arrows 9. In this well known manner, the drilling fluid 26 lubricates the drill bit 2 and carries formation cuttings up to the surface as it is returned to the pit 27 for recirculation.

The bottom hole assembly 1 of the illustrated example implementation includes a logging-while-drilling (LWD) module 4, a measurement-while-drilling (MWD) module 5, a rotary-steerable system and motor 6 (e.g., a directional drilling subsystem), and the drill bit 2.

The LWD module 4 is housed in a special type of drill collar, as is known in the art, and can contain one or a plurality of known types of logging tools. It will also be understood that more than one LWD and/or MWD module can be employed, e.g., as represented at 7. (References, throughout, to a module at the position of 5 can alternatively mean a module at the position of 7 as well.) The LWD module 4 includes capabilities for measuring, processing, and storing information, as well as for communicating with the MWD module 5. In the present embodiment, the LWD module 4 includes a fluid property sensor.

The MWD module 5 is also housed in a special type of drill collar, as is known in the art, and can contain one or more devices for measuring characteristics of the drill string and drill bit. The MWD module 5 further includes an apparatus (not shown) for generating electrical power to the downhole system. This may typically include a mud turbine generator powered by the flow of the drilling fluid, it being understood that other power and/or battery systems may be employed. In the present embodiment, the MWD module 5 includes one or more of the following types of measuring devices: a weight-on-bit measuring device, a torque measuring device, a vibration measuring device, a shock measuring device, a stick slip measuring device, a direction measuring device, and/or an inclination measuring device. The MWD module 5 further includes capabilities for communicating with surface equipment.

A use of the example methods and apparatus described herein is in conjunction with controlled steering or "directional drilling" using the rotary-steerable subsystem 6. Directional drilling is the intentional deviation of the wellbore from the path it would naturally take. In other words, directional drilling is the steering of the drill string so that it travels in a desired direction. Directional drilling comprises geometrical steering, in which the drill bit is typically steered along a pre-determined path in an Earth formation, and geological steering, in which the drill bit is typically steered relative to geological features of the Earth formation. Directional drilling is, for example, advantageous in offshore drilling because it enables many wells to be drilled from a single platform. Directional drilling also enables horizontal drilling through a reservoir. Horizontal drilling enables a longer length of the wellbore to traverse the reservoir, which increases the production rate from the well. A directional drilling system may also be used in vertical drilling operations as well. Often the drill bit 2 will veer off of a planned drilling trajectory because of the unpredictable nature of the formations being penetrated or the varying forces that the drill bit 2 experiences. When such a deviation occurs, a directional drilling system (e.g., the rotary-steerable subsystem 6) may be used to put the drill bit 2 back on course.

A known method of directional drilling includes the use of a rotary steerable system ("RSS"). In an RSS, the drill string 12 is rotated from the surface, and downhole devices cause the drill bit 2 to drill in the desired direction. Rotating the drill string 12 greatly reduces the occurrences of the drill string 12 getting hung up or stuck during drilling. Rotary steerable drilling systems for drilling deviated boreholes into the earth may be generally classified as either "point-the-bit" systems or "push-the-bit" systems. In the point-the-bit system, the axis of rotation of the drill bit 2 is deviated from the local axis of the bottom hole assembly 1 in the general direction of the new hole. The hole is propagated in accordance with the customary three point geometry defined by upper and lower stabilizer touch points and the drill bit 2. The angle of deviation of the drill bit 2 axis coupled with a finite distance between the drill bit 2 and a lower stabilizer results in the non-collinear condition required for a curve to be generated. There are many ways in which this may be achieved including a fixed bend at a point in the bottom hole assembly 1 close to the lower stabilizer or a flexure of the drill bit 2 drive shaft distributed between an upper and the lower stabilizer. In its idealized form, the drill bit 2 is not required to cut sideways because the bit axis is continually rotated in the direction of the curved hole. Examples of point-the-bit type rotary steerable systems, and how they operate are described in U.S. Patent Application Publication No. 2001/0052428 and U.S. Pat. Nos. 6,401,842; 6,394,193; 6,364,034; 6,244,361; 6,158,529; 6,092,610; and 5,113,953, all of which are hereby incorporated herein by reference in their entireties.

In the push-the-bit rotary steerable system there is usually no specially identified mechanism to deviate the bit axis from the local bottom hole assembly axis; instead, the requisite non-collinear condition is achieved by causing either or both of an upper or a lower stabilizer(s) to apply an eccentric force or displacement in a direction that is preferentially orientated with respect to the direction of hole propagation. Again, there are many ways in which this may be achieved, including non-rotating (with respect to the hole) eccentric stabilizers (displacement based approaches) and eccentric actuators that apply force to the drill bit in the desired steering direction. Again, steering is achieved by creating non co-linearity between the drill bit 2 and at least two other touch points. In some instances, the drill bit 2 is required to cut side ways to generate a curved hole. Examples of push-the-bit type rotary steerable systems, and how they operate are described in U.S. Pat. Nos. 5,265,682; 5,553,678; 5,803,185; 6,089,332; 5,695,015; 5,685,379; 5,706,905; 5,553,679; 5,673,763; 5,520,255; 5,603,385; 5,582,259; 5,778,992; 5,971,085, all of which are hereby incorporated herein by reference in their entireties.

Figure 1B:
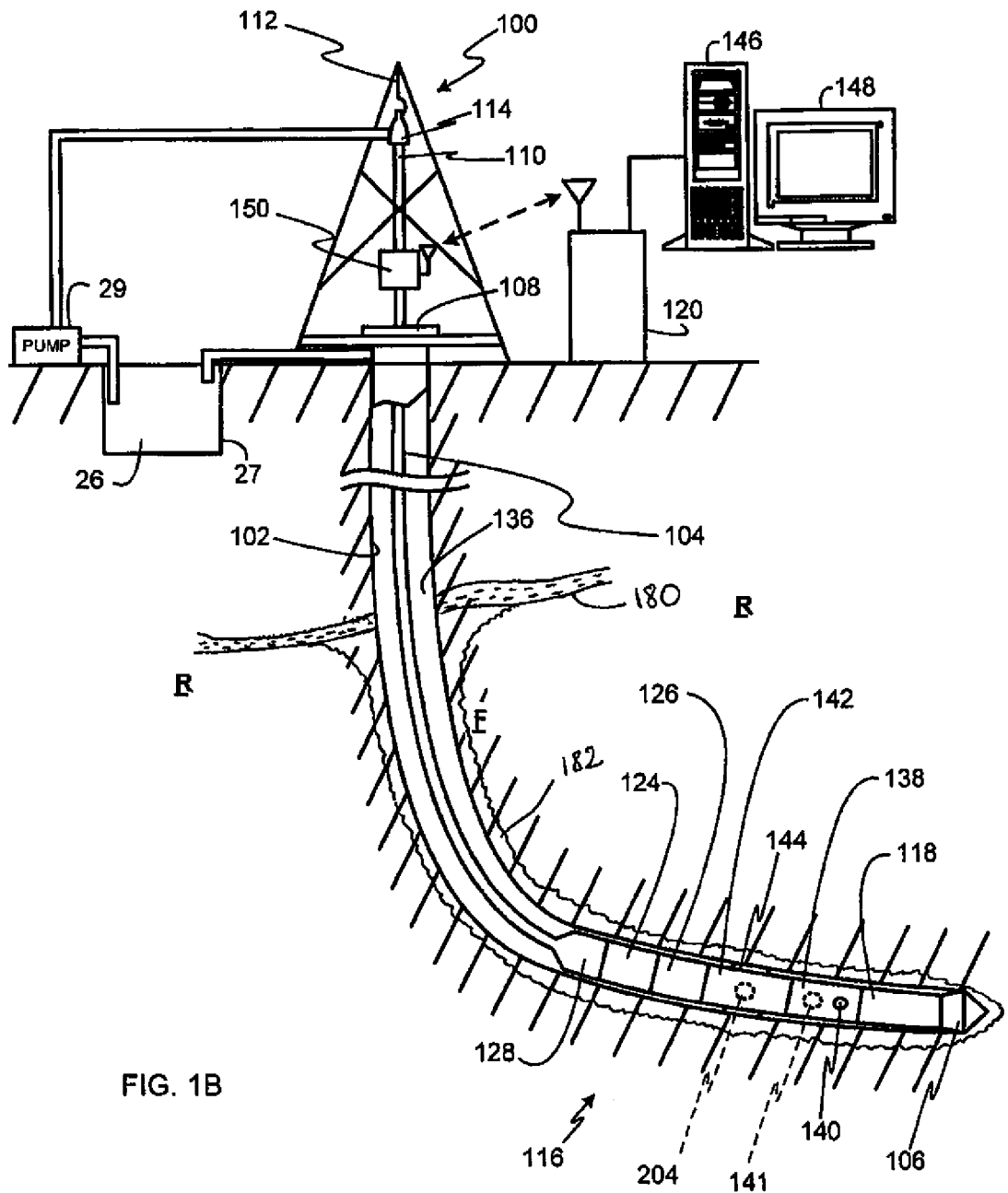
FIG. 1B is an elevation view of another wellsite system that may be used to implement the example methods and apparatus described herein.

FIG. 1B is an elevational view of another wellsite system that may be used to implement the example methods and apparatus described herein. In the illustrated example, a platform and derrick assembly 100 are positioned over a well 102 (e.g., a wellbore or borehole) penetrating a subsurface formation F in a reservoir R. Although the platform and derrick assembly 100 are shown as a land-based rig, the example methods and apparatus described herein are not limited for use with land-based rigs. A drill string 104 is suspended within the well 102 and includes a drill bit 106 at its lower end. The drill string 104 is rotated by a rotary table 108, energized by means not shown, which engages a kelly 110 at the upper end of the drill string 104. The drill string 104 is suspended from a hook 112, attached to a traveling block (not shown), through the kelly 110 and a rotary swivel 114, which permits rotation of the drill string 104 relative to the hook 112. In the illustrated example, the well 102 is formed using directional drilling.

The drill string 104 further includes a bottom hole assembly (BHA) 116 coupled to the drill bit 106. The BHA 116 includes a directional drilling subassembly 118 to adjust the drilling direction of the drill bit 106 based on control signals received from, for example, a surface logging and control system 120. The BHA 116 includes capabilities for measuring, processing, and storing information, as well as communicating with surface equipment. In the illustrated example, the BHA 116 includes, among other things, a telemetry and measurement while drilling (MWD) tool 124 (i.e., a survey tool). The MWD tool 124 is configured to send direction and inclination data to the surface and track the actual well trajectory of the well 102. The MWD tool 124 is also used to perform two-way telemetry between the surface system 120 and downhole components of the BHA 116. For example, the MWD tool 124 can be used to receive commands from the surface system 120 related to collecting fluid samples from the well 102 and/or measuring the fluid samples.

In the illustrated example, the BHA 116 is provided with a logging while drilling (LWD) tool 126 (i.e., a formation evaluation tool). Although one LWD tool 126 is shown, in other example implementations, the BHA 116 can be provided with any number of LWD tools. The LWD tool 126 is used to obtain formation evaluation logs of the well 102 and improve the petrophysical knowledge of the reservoir R while the well 102 is being drilled. The LWD tool 126 and any other LWD tool provided to the BHA 116 may be any combination of, for example, a Nuclear Magnetic Resonance (NMR) tool (e.g., the proVISION™ nuclear magnetic resonance while drilling tool provided by Schlumberger Technology Corporation), a nuclear spectroscopy tool for obtaining lithology and porosity information (e.g., the EcoScope™ formation evaluation tool provided by Schlumberger Technology Corporation), a sonic tool (e.g., the sonicVISION™ sonic while drilling tool provided by Schlumberger Technology Corporation), a seismic tool (e.g., the seismicVISION™ seismic while drilling tool provided by Schlumberger Technology Corporation), an acoustic imaging tool, and/or a resistivity imaging tool (e.g., the geoVISION™ resistivity imaging tool and the PeriScope 15™ deep-reading resistivity tool both provided by Schlumberger Technology Corporation).

To communicate measurement information associated with the formation F surrounding the well 102 and the reservoir R to the surface system 120 and to receive direction drilling control signals, the bottom hole assembly 116 is provided with a telemetry system 128 that may include, preferably but not necessarily, wired pipes (not shown). A telemetry system that may be used to implement the example telemetry system 128 is described in detail in U.S. Patent Application Publ. No. 2007/0029112, which is hereby incorporated herein by reference in its entirety. For example, a wireless data transceiver 150 can be coupled to the drill string 104 as shown in FIG. 1B to exchange data between the surface logging control system 120 and the BHA 116. However, other telemetry systems, such as two ways mud pulse telemetry systems, may alternatively or additionally be used.

In the illustrated example, the BHA 116 includes a downhole mud gas logging tool 138. The downhole mud gas logging tool 138 has an inlet 140 for receiving fluids from the annulus 136. A portion of the fluids received in the downhole mud gas logging tool 138 via the inlet 140 includes formation fluid that has been released into the drilling mud as the formation rock was crushed during drilling. The mud gas logging tool 138 is capable of separating volatiles (e.g., hydrocarbons of low molecular weight) from the received fluids and in the process generating gas using, for example, a volume expansion and/or heating process. In the illustrated example, the downhole mud gas logging tool 138 is provided with a gas sensor 141 to measure the composition of the separated gases. The composition of the separated gases may be analyzed using any suitable composition analysis device including, for example, a mass spectrometer or a gas chromatographer. In addition, downhole mud gas logging preferably distinguishes between "background" concentration of hydrocarbon in the mud and "incoming" concentration originating from the rock being drilled by periodically measuring and accounting for "background" concentration of hydrocarbon in the mud.

Although many types of hydrocarbons and hydrocarbon structures exist in a reservoir, mud gas logging may only measure a subset of data (e.g., data indicative of the most volatile components contained in the formation fluid) that can otherwise be acquired using other techniques such as, for example, sidewall sampling. Indeed, mud gas logging looks only at a subset of the hydrocarbons and gases usually encountered in Earth formations (e.g., volatile hydrocarbons, carbon dioxide, hydrogen sulphide, nitrogen, etc.) and typically excludes those components that are trapped in the drill cuttings or are present in the drilling fluid 26 but are not easily volatilized (e.g., those components which have molecular weights at least as large as those of the components of synthetic oil-based muds). However, in contrast to sidewall sampling which involves halting drilling operations at least momentarily, mud gas logging involves nearly continuous data acquisition along a well as the well is being drilled without needing to stop the drill string. In this way, the mud gas logging data can be used to determine partial but almost continuous representations of a reservoir fluid while a well is being drilled. Further, based on the hydrocarbon concentration measurements (e.g., a ratio of concentration of hydrocarbon types), mud gas logging can be used to determine changes in the type of formation fluids that are expected to be found as soon as a new formation is being drilled.

To acquire relatively quantitative mud gas logging data, the mud gas logging tool 138 is operated in connection with calibration data. The mud gas logging calibration data is generated based on known characteristics or fluid properties of a well. In the illustrated examples described herein, the mud gas logging calibration data is determined, at least in part, based on sidewall sampling data (e.g., sidewall sample measurements acquired by the sampling while drilling tool 142 described below). As discussed below in connection with the example process of FIGS. 4A and 4B, the mud gas logging calibration data can be checked against actual fluid sample measurements acquired using sidewall sample measurements to determine whether the mud gas logging calibration should be adjusted. Hydrocarbon measurements acquired using a sampling while drilling tool represent snapshots of the fluid in the formation F from different locations. The hydrocarbon measurements are then used to determine what type of fluid is expected to be present in the formation. The sidewall sampling measurements then confirm whether the fluid type estimations made using the hydrocarbon data provided by the mud gas logging tool 138 are quantitatively correct or within an accuracy threshold. If so, the mud gas logging data is deemed to be correct (or does not require adjustment). Otherwise, the mud gas logging calibration data is adjusted to enable the mud gas logging tool 138 to generate mud gas logging data that is in agreement with the sidewall fluid sample measurements.

A downhole mud gas logging tool that may be used to implement the mud gas logging tool 138 is describe in U.S. Pat. No. 7,458,257, which is hereby incorporated herein by reference in its entirety. In some example implementations, a surface mud gas logging unit may be used in addition to or instead of the downhole mud gas logging tool 138.

In the illustrated example, the bottom hole assembly 116 includes a sampling while drilling tool 142. The sampling while drilling tool 142 includes a probe 144 to engage a surface of the well 102 to draw fluids from the reservoir R. In other example implementations, straddle packers (not shown) can additionally or alternatively be used to engage and isolate a portion of the surface of the well 102 to draw fluids from the reservoir R.

To determine sampling locations in the formation F, the sampling while drilling tool 142 may be operated in connection with a continuous representation of a reservoir fluid along the well trajectory. In some example implementations, the continuous representations of a reservoir fluid along the well trajectory may be provided by data generated by the mud gas logging tool 142. For example, as described earlier, the mud gas logging tool 142 is capable of providing almost continuous representations of a reservoir fluid while a well is being drilled. Thus, based on a ratio of concentrations of hydrocarbon types measured by the mud gas logging tool 142, changes in the type of formation fluids that are expected to be found can be identified as soon as a new formation is being drilled. The location of such a change may be used to set the sampling tool probe in the suspected new formation. The sampling tool may then draw and analyze formation fluid from the new formation and provide a more complete description of the fluid in that formation.

Figure 2:
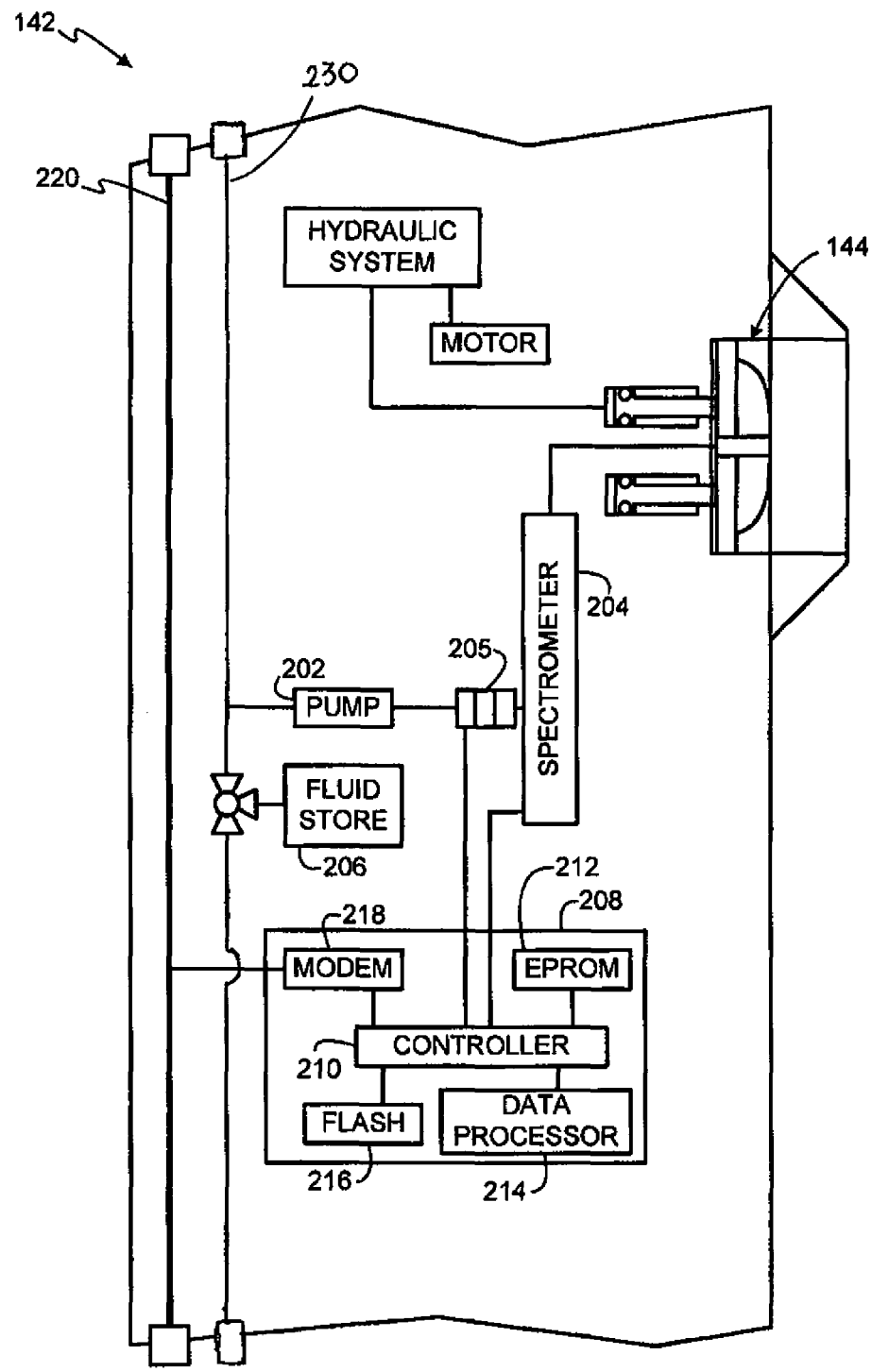
FIG. 2 is an example block diagram of a sampling while drilling tool of the drill string of FIG. 1B.

An example detailed block diagram of the sampling while drilling tool 142 is shown in FIG. 2. In the illustrated example of FIG. 2, the sampling while drilling tool 142 is provided with a pump 202 that draws fluids from the formation F into the tool 142. The pump 202 can be controlled to withdraw sufficient fluid from the reservoir R so that contamination-free reservoir fluid properties can be estimated. That is, during an initial pumping phase, the pump 202 may draw a mixture of formation fluid and the drilling fluid 26 that has invaded the formation F (see filtrate invaded zone 182 in FIG. 1B), which is a contaminant in the formation fluid. After some time, the fluid drawn by the pump 202 has a reduced fraction of contaminants (e.g., invaded drilling fluid 26 into the formation F), and measurements on pristine formation fluid can be performed. In some example implementations in which contaminants remain in the drawn formation fluid, computational filtering processes can be performed on the fluid sample measurement data to determine fluid properties of otherwise pristine fluid samples based on the contaminated samples. For example, to determine fluid optical density, a convex combination of optical densities from different fluid samples can be used to determine the fluid optical density of a pristine sample. To determine viscosity, a mixing rule such as, for example, a refinery (e.g., quarter power) formula or the Grundbarg-Nissan mixing rule can be applied to the measured fluid data. To determine fluid composition, a subtraction or skimming method can be used in combination with an equation of state to determine the fluid composition of a pristine sample. In the illustrated examples described herein, these types of corrections for contaminated fluid samples are performed in real time when well trajectory adjustments are determined in real time.

The sampling while drilling tool 142 also includes one or more fluid sensors to measure the reservoir fluid drawn into the tool 142. In the illustrated example, the sampling while drilling tool 142 is provided with a spectrometer 204. The spectrometer 204 may be implemented using, for example, a light absorption/fluorescence spectrometer, a NMR spectrometer, or a mass spectrometer. In other example implementations, the sampling while drilling tool 142 may be provided with a gas chromatographer (e.g., to perform one-dimensional or two-dimensional gas chromatography measurements) in addition to or instead of the spectrometer 204. In the illustrated example, the sampling while drilling tool 142 is also provided with one or more sensors 205 to measure pressure/temperature, density/viscosity, and/or any other fluid properties. The sampling while drilling tool 142 may optionally include one or more fluid store(s) 206 connected to a tool fluid bus 230, each store including one or more fluid sample chambers in which reservoir fluid recovered during sampling operations can be stored and brought to the surface for further analysis and/or confirmation of downhole analyses.

To store, analyze, process, and/or compress test and measurement data (or any other data acquired by the sampling while drilling tool 142), the sampling while drilling tool 142 is provided with an electronics system 208. In the illustrated example, the electronics system 208 includes a controller 210 (e.g., a CPU and random access memory) to control operations of the sampling while drilling tool 142 and implement measurement routines (e.g., to control the spectrometer 204, etc.). To store machine accessible instructions that, when executed by the controller 210, cause the controller 210 to implement measurement processes or any other processes, the electronics system 208 is provided with an electronic programmable read only memory (EPROM) 212. In the illustrated example, the controller 210 is configured to receive digital data from one or more sensors (e.g., the spectrometer 204 and the sensors 205) provided in the sampling while drilling tool 142.

To analyze measurement data, the sampling while drilling tool 142 is provided with a data processor 214. In the illustrated example, the data processor 214 is configured to determine fluid properties (e.g., fluid composition, GOR, saturation pressures, formation mobility, fluid color, asphaltene or wax concentration levels, pressure, temperature, density, viscosity, compressibility, EoS parameters, thermal and chemical properties, etc. . . . ) of formation fluid samples based on the measurement data collected by the spectrometer 204 and/or the one or more sensors 205. To store measurement data, analysis data, or any other kind of data, acquired, collected, and/or generated by the sampling while drilling tool 142 using, for example, the spectrometer 204, the controller 210, and/or the data processor 214, the electronics system 208 is provided with a flash memory 216. To communicate information when the sampling while drilling tool 142 is downhole, the electronics system 208 is provided with a modem 218 that is communicatively coupled to an electrical tool bus 220 communicatively coupled to the surface logging and control system 120 (FIG. 1B). In the illustrated example, the modem 218 enables the surface logging and control system 120 to retrieve measurement and/or analysis data stored in the flash memory 216.

In example implementations in which the BHA 116 uses mud-pulse telemetry, the flash memory 216 preferably, but not necessarily, includes sufficient memory capacity to store all or essential segments of sensor measurement data and interpreted or analysis results computed by the sampling while drilling tool 142. In addition, the data processor 214 preferably, but not necessarily, has sufficient processing power and the appropriate algorithms or data analysis routines to generate and store useable information based on the sensor measurement data. For example, the data processor 214 can be configured to process the sensor measurement data to generate, for example, fluid composition and the fluid constituent uncertainties, which may be compressed and relayed to the surface system 120 so that real-time decisions can be made to determine a well trajectory of the well 102 (FIG. 1B). In example implementations in which relatively high-bandwidth communications (e.g., wired communications via the electrical tool bus 220 of the wired drill string 104 (FIG. 1B)) are available, the modem 218 can communicate the sensor measurement data to the surface system 120, and the surface system 120 can process and analyze the sensor measurement data.

Although the components of FIG. 2 are shown and described above as being communicatively coupled and arranged in a particular configuration, the components of the sampling while drilling tool 142 can be communicatively coupled and/or arranged differently than depicted in FIG. 2 without departing from the scope of the present disclosure. For example, each of the processor 214 and the controller 210 (and/or processors in the surface logging and control system 120 and the computer 146 of FIG. 1B) may be any suitable processor, processing unit, microprocessor, and/or controller. The electronics system 208 may be a multi-processor system (and/or multi-controller system) and, thus, may include one or more additional processors (and/or one or more additional controllers) that are identical or similar to the processor 214 (and/or controller 210). In addition, the example methods, apparatus, and systems described herein are not limited to a particular conveyance type but, instead, may be implemented in connection with different conveyance types including, for example, coiled tubing, wireline retrievable, wired-drill-pipe, and/or other conveyance means known in the industry.

Returning to FIG. 1B, although the example BHA 116 is shown as having the mud gas logging tool 138 and the sampling while drilling tool 142, in some example implementations, the BHA 116 may be provided with the mud gas logging tool 138 but not the sampling while drilling tool 142 or may be provided with the sampling while drilling tool 142 but not the mud gas logging tool 138.

As shown in FIG. 1B, the surface logging and control system 120 is communicatively coupled to a computer 146 including a terminal display/input console 148 to enable an operator to monitor and interact with drilling operation associated with the drill string 104. While the computer 146 and the terminal display/input console 148 are depicted as being located on the platform and derrick assembly 100, they can be remotely located from the platform and derrick assembly 100 and may communicate with the drill string 104 via any communication link known in the art.

FIG. 3A depicts a block diagram of an example apparatus 300 that may be used to analyze well data to control a drill string (e.g., the drill string 104 of FIG. 1B) to form a well (e.g., the well 102 of FIG. 1B). In particular, the example apparatus 300 is configured to receive measurement and/or analysis data from the BHA 116 of FIG. 1B, analyze the received data, and control a well trajectory of the well 102 by controlling the direction of drilling of the BHA 116. In some example implementations, the example apparatus 300 can be used to adjust the well trajectory to optimize characterization of the reservoir R (FIG. 1B). The example apparatus 300 can additionally or alternatively be used to adjust the well trajectory to optimize the drainage/production of the reservoir R.

The example apparatus 300 may be implemented in the BHA 116, the surface logging and control system 120, the surface computer 146, or in any combination thereof using any desired combination of hardware, firmware, and/or software. For example, one or more integrated circuits, discrete semiconductor components, or passive electronic components may be used. Additionally or alternatively, some or all of the blocks of the example apparatus 300, or parts thereof, may be implemented using instructions, code, and/or other software and/or firmware, etc. stored on a machine accessible medium that, when executed by, for example, a processor system (e.g., the example surface logging and control system 120 (FIG. 1B), the computer 146 (FIG. 1B), and/or the example electronics system 208 of FIG. 2), perform the operations represented in the flow diagrams of FIGS. 4A, 4B, and 5-9. Although the example apparatus 300 is described as having one of each block described below, the example apparatus 300 may be provided with two or more of any block described below. In addition, some blocks may be disabled, omitted, or combined with other blocks.

Turning to FIG. 3A in detail, the example apparatus 300 includes a reservoir geological model database 302 to store a reservoir geological model. The example apparatus 300 also includes a formation evaluation logs database 304 to store formation evaluation logs corresponding to wells previously drilled in the reservoir R and/or to a well (e.g., the well 102) currently being drilled. To store well trajectories (corresponding to previous wells and the current well), the example apparatus 300 is provided with a well trajectory database 306. The example apparatus 300 is also provided with a fluid analysis report database 308 to store fluid analysis reports corresponding to laboratory analyses of fluid samples collected in previous wells. The fluid analysis report database 308 also stores in-situ fluid analysis data collected in previous wells and the current well. In addition, the fluid analysis report database 308 may be used to store one or more sensor calibration(s) (e.g., mud gas logging calibration data).

Reservoir geological model data stored in the reservoir geological model database 302 describes the locations of sedimentary layers, faults, etc. in the reservoir R (FIG. 1B). The geological model can be generated using one or more seismic, electro-magnetic, gravity, or other surveys of the reservoir R, for example, prior to drilling a well (e.g., the well 102 of FIG. 1B). Preferably, but not necessarily, the reservoir geological model database 302 also stores information relating to depositional sequences and reservoir structural information obtained from well image data such as, for example, gamma ray image data, density image data, and/or resistivity image data.

In some example implementations, formation evaluation logs of one well can include measurement data acquired in neighboring or offset wells. Formation evaluation log data stored in the formation evaluation logs database 304 can be obtained while drilling (e.g., using the drill string 104 of FIG. 1B) or after drilling (e.g., using a wireline tool) to determine the physical and chemical properties (e.g., petrophysical characteristics) of formations to better model subsurface fluid reservoirs. In the illustrated example, the formation evaluation logs include one or more of natural gamma ray data, resistivity data, porosity data, and density data. The data stored in the formation evaluation log database is preferably, but not necessarily, collected using tools which have at least the capabilities of tools referred to as "triple combo" tools that include, for example, a resistivity tool, a neutron porosity tool, and a nuclear density tool.

The formation evaluation logs may additionally or alternatively include spectroscopy data (e.g., nuclear spectroscopy data or NMR spectroscopy data). In the illustrated example, the formation evaluation logs preferably, but not necessarily, include formation pressure/temperature data points acquired in one or more offset wells formed in the reservoir R (FIG. 1B). If pressure data (from, for example, neighboring wells) is not available prior to drilling the current well (e.g., the well 102 of FIG. 1B), pressure data may be acquired while drilling the current well using, for example, the sampling while drilling tool 142 (FIGS. 1B-3B). The formation evaluation logs may also store drilling events indicative of, for example, a mud loss, a mud weight, a weight on bit, a rate of penetration, etc.

Fluid analysis reports stored in the fluid analysis report database 308 include data indicative of fluid compositions and thermo physical properties (e.g., temperature, pressure, volume, compressibility, density, viscosity, formation volume factor, gas-oil ratio, API gravity, phase envelope, thermal capacity, etc.) of fluids drawn from the reservoir R. The fluid analysis data can be used to determine how fluid properties vary along different depths of a formation and different portions of a reservoir. Fluid composition can be measured in-situ or in a laboratory environment. In-situ fluid analysis (i.e., downhole fluid analysis) data can include data in the fluid analysis reports indicative of concentration levels of methane $C1$, ethane $C2$, $CO2$, and water $H2O$. In addition, the in-situ fluid analysis data can include concentration levels of fluid components such as, for example, the lumped group of propane, butane, and pentane $C3-5$ and the lumped group of hydrocarbons with 6 or more carbons in their molecules $C6+$. Gas-oil ratios of hydrocarbons can be derived from the fluid composition data. In addition, in-situ fluid analysis data can also include formation fluid pressure data, and fluid color related to, for example, concentration levels of asphaltene. In-situ fluid analysis data may also include density and viscosity of the sampled fluid.

In a laboratory environment (e.g., at the surface) fluid composition can be analyzed up to hydrocarbon chains having 45 carbon atoms ($C45$), and sometimes longer chains. Other data in the fluid analysis reports that can be determined in a laboratory environment include gas-oil ratio (GOR) data, saturate aromatic resin asphaltene (SARA) analysis data, and flow assurance parameters such as, for example, asphaltene onset pressure, wax appearance/precipitation temperature (e.g., cloud point), and phase transition boundaries. Particular types of laboratories such as, for example, geochemistry laboratories can be used to perform relatively more specialized analyses including, for example, analysis of heavy metals, sulfurs, carbon isotopes, and crude oil fingerprinting. These specialized analyses can be used to investigate the origin of oil in a fluid and identify areas of reservoir compartmentalization (for example, geological segmentation of reservoirs into isolated compartments).

In the illustrated example, the example apparatus 300 is provided with a petrophysics simulator 310 to determine distributions of porosity, lithology and fluid content along the well 102 corresponding to the formation evaluation log data. In the illustrated example, the petrophysics simulator 310 receives data from the formation evaluation logs database 304 to determine or simulate porosity, lithology, and fluid content data corresponding to the reservoir R based on the log information of the formation F and stored in the formation evaluation logs database 304. In some example implementations, the fluid content data determined by the petrophysics simulator 310 represents a "black oil model" that includes coarse data indicative of proportions of water, oil and free gas without distinguishing between, for example, the type (e.g., the composition) of the oil. In the illustrated example, the DecisonXpress™ petrophysical evaluation system developed and sold by Schlumberger Technology Corporation can be used to implement the petrophysics simulator 310.

To refine the description of the reservoir fluid determined by the petrophysics simulator 310 (e.g., C1, C2, C3-C5, C6+, and/or asphaltene concentrations) and, in particular, to determine the spatial distribution of the components of hydrocarbons, or other fluids, along the well, the example apparatus 300 is provided with a fluid simulator 312. In the illustrated example, the fluid analysis report data from the fluid analysis report database 308 is communicated to the fluid simulator 312. In addition, the parameters used in the fluid simulator 312 to parameterize the variation of fluid composition within the individual flow units or segments of the well, may be used together with their associated uncertainties to perform comparisons between fluids in different flow units to determine how fluid properties or fluid characteristics change between the different flow units.

In some example implementations, the fluid simulator 312 can be configured to determine an equation of state (EoS) from data stored in the fluid analysis reports. An EoS simulator determines an equation of state (e.g., the Peng-Robinson EoS) that relates oil composition, temperature, volume and pressure to represent the thermodynamic behavior of each fluid sample. The EoS can be used to compute fluid composition variations (e.g., concentrations of methane C1, the lumped group of hydrocarbons with 6 or more carbons C6+, asphaltene, etc.) in the flow unit, segment, or interval to which the fluid sample belongs. Typically, a flow unit is a rock or material volume in which the fluid may freely migrate. By segmenting each well (e.g., the well 102) according to the flow units through which it passes and determining at least one equation of state in each flow unit, the fluid simulator 312 can be used to determine a hydrocarbon composition distribution along the entire well. In the illustrated example, the PVT Pro™ EoS simulation tool developed and sold by Schlumberger Technology Corporation can be used to implement the fluid EoS simulator of the fluid simulator 312, or the PVTi™ EoS tool developed and sold by Schlumberger Technology Corporation can be used to implement the fluid simulator 312.

In yet other example implementations, one or more properties measured along the well 102 using in-situ fluid analysis sensors are stored in a fluid analysis database 308 and are communicated to the fluid simulator 312. The fluid simulator 312 determines (e.g., by surface fitting, by employing neural network techniques or other well known methods) a trend in the measured property(ies) and extrapolates this trend along each flow unit or segment of a well.

In the illustrated example, the example apparatus 300 is provided with a reservoir simulator 314 which generates a fluid composition distribution across an entire reservoir. Specifically, when fluid composition data is obtained (e.g., using the petrophysics simulator 310 and/or the fluid simulator 312) along a plurality of wells in a reservoir, the reservoir simulator 314 can arrange the fluid composition data to generate a fluid composition distribution for that reservoir. In the illustrated example, the reservoir simulator 314 is configured to use the features of the geological model stored in the reservoir geological model database 302 to populate the entire simulated reservoir in an empirical manner. That is, as the geological model data improves or more geological model data is acquired using, for example, fluid sample measurements or other types of measurements, the reservoir simulator 314 can update the fluid composition distribution or fluid map of the reservoir R.

The reservoir simulator 314 may be a finite difference, a finite element, a finite volume or a streamline simulator that solves the equations governing the distribution of fluids and their fluid components at the scale of the reservoir R under constraints imposed by the fluid compositions measured along each well. In the illustrated example, the grid blocks of the reservoir simulator 314 should not be too coarse, but should instead be fine enough to capture the level of variation suitable for controlling drilling operations. The parameters (e.g., temperature gradient, capillary pressure curves, etc.) associated with equations governing the fluid distribution can be determined from prior knowledge (e.g., prior measurement data and/or analysis data of the reservoir R stored in, for example, the formation evaluation logs database 304, including, but not limited to, nuclear magnetic resonance and/or core data acquired in offset wells). Additionally, or alternatively, the petrophysics simulator 310 can determine the water saturation profile across a water-oil contact in the reservoir R from the formation evaluations logs database 304 and determine capillary pressure curves based on the water saturation profile data and sandface pressure measurements acquired with a sampling while drilling tool 142. In the illustrated example, the capillary pressure curves can in turn be used by the reservoir simulator 314 to determine water saturation levels away from the wellbore. In some example implementations, the ECLIPSE™ reservoir simulator tool developed and sold by Schlumberger Technology Corporation can be used to implement the reservoir simulator 314.

In some example implementations, an EoS determined by the fluid simulator 312 may also be used to populate the fluid composition distribution over a simulated reservoir where the fluid is suspected to be in thermodynamic equilibrium and where the crude oil may be treated as a true molecular solution.

In other example implementations, stochastic processes conditioned to measurements made at key or select wells may be used to simulate a reservoir and populate the composition distribution over the simulated reservoir.

In some example implementations, models of non equilibrium distributions of hydrocarbons can be used to analyze actual reservoir fluids and populate the composition distribution over the simulated reservoir. Non equilibrium distributions occur when reservoir fluids deviate from equilibrium, which can happen for different reasons. For example, reservoir fluids can deviate from equilibrium due to different factors including biodegradation, thermal gradients, current reservoir charging, charge history coupled with slow mixing kinetics, water/gas washing, leaky seals, and/or miscible floods. Typically, these factors can be modeled using an adjusted static model. In some instances, if one of the factors dominates the disequilibrium, that factor can be modeled with a simple parameter or set of parameters. For example, an empirical model can be used to find a linearly increasing contribution of biodegradation increasing towards an oil-water contact.

In other example implementations, Archimedes buoyancy in Boltzmann equation shown in equation 1 below can be used to populate the asphaltene concentration level over a reservoir and/or to determine the expected optical density (OD) in the visible range resulting from the asphaltene concentration level. For example, measurements may be conducted to detect asphaltene concentration levels in fluid samples and develop fluid models based on those asphaltene concentration levels. Asphaltenes are often present in crude oil as a nano-colloidal suspension, especially in highly under-saturated black oils. Asphaltene concentration is measurable using optical fluid analysis and, thus, one can determine if a black oil encountered is the expected black oil. That is, in drilling a new well, one can first predict and then perform measurements in real time to determine whether the black oil encountered in any flow unit or segment has the asphaltene content expected based on a fluid model of the reservoir previously developed using, for example, equation 1 below.

$$OD(h)/OD(0)=\exp\{-V\Delta\rho gh/kT\}$$  Equation 1

In equation 1 above, OD(h) is the optical density or color of the oil at a height (h) induced by the asphaltene content, (V) is the volume of the asphaltene colloidal particle (found to be ~16 Å for black oils), ( ) is the density contrast between asphaltene and the bulk oil, (g) is the Earth's gravitational constant, (k) is the Boltzmann's constant, and (T) is the temperature. For compressible oils, a semi-empirical methodology could alternatively be employed to describe the asphaltene concentration in those compressible oils.

In the illustrated example, the example apparatus 300 is provided with a reservoir fluid map database 316 to store maps of fluid content (e.g., oil, water, gas) and the fluid composition maps of at least one of oil, water, or gas for subsequent use to determine well trajectories. For example, a reservoir fluid map data stored in the reservoir fluid map database 316 may be used when simulating production corresponding to two hypothetical production well trajectories. In such a case, the reservoir fluid map data is used to populate input data for prediction modules 315 including a well production simulator 318 and/or a tool response simulator 320. In the illustrated examples described herein, the reservoir fluid maps can include data corresponding to portions of basin models generated using the reservoir simulator 314. A basin denotes a depression in the Earth's crust in which sediments accumulate. If hydrocarbon source rocks or material occur in combination with appropriate depth and duration of burial, then a petroleum system can develop within the basin. A basin model is a model that may account for the evolution of hydrocarbons from a source rock and their transformation with temperature and time, may model the migration and accumulation of hydrocarbons within the confines and structural features of the basin, and may allow the estimation of the associated uncertainty levels in the predictions of the reservoir simulator 314 across the geologic ages. Where reservoir fluid maps include basin simulated data, the reservoir fluid maps would represent the result of the simulated basin for the present days near the time frame during which measurements are acquired to determine well trajectories. A more detailed discussion of how the reservoir simulator 314 simulates basin data is presented below in connection with FIG. 3B.

As shown in FIG. 3A, the example apparatus 300 is provided with the well production simulator 318 to predict a well's production by simulating a multiphase production flow in at least a portion of the reservoir surrounding a currently drilled well (e.g., the well 102 of FIG. 1B). For example, the well production simulator 318 can utilize other data relating to relative permeabilities, end point saturations (e.g., bound water fraction), and capillary pressure curves determined by, for example, the petrophysics simulator 310. In addition, the well production simulator 318 can utilize formation pressure/temperature data, fluid mobility data acquired while sampling, drilling related information, mud filtrate invasion (see for example invaded zone 182 of FIG. 1B) data (which may be deduced from open-hole logs), and NMR data from the formation evaluation logs database 304. The reservoir simulator 314 can use these properties in connection with the geological trends described by the geological model stored in the reservoir geological model database 302 to generate a visual three-dimensional volume around the drilled well 102. Thus, the well production simulator 318 can use the generated three-dimensional volume to predict how much hydrocarbon can be recovered for each hypothetical well trajectory, and the well trajectory to be formed by the drill string 104 (FIG. 1B) can be selected based on the drainage of the reservoir R it provides. In the illustrated example, the well production simulator 318 can be implemented using the SWPM™ (Single Well Predictive Modeling) tool developed and sold by Schlumberger Technology Corporation.

Alternatively or additionally, the fluid map data stored in the reservoir fluid map database 316 can be used to predict a reservoir fluid log along the trajectory of a well. In this case, the fluid and geology map data from the reservoir map database 316 is communicated to the tool response simulator 320 that is configured to generate visual representations of the formation evaluation log data measured by the logging while drilling subsystem 126 and stored in the formation evaluation logs database 304 as the well 102 is being drilled. In the example implementations described herein, vertical well intersections are created along the well trajectory paths to create "well curtain sections" used to visualize the position of the well trajectory paths relative to seismic sections, faults, formation dips, marker beds, and/or other geologic features or properties of a reservoir. Thus, in the illustrated example, the tool response simulator 320 can determine predicted log data along a particular intersection with a well trajectory using composition information stored in the reservoir fluid map database 316. The predicted log data represents log data (e.g., optical spectroscopy absorbances in predetermined wavelength in the visible, near infrared range in the case of an optical spectrometer, mass spectra in the case of a mass spectrometer, or gas chromatography measurements) that would be acquired by fluid sensors (e.g., the spectrometer 204, a gas chromatographer, and/or the sensors 205 of FIG. 2) implemented in a drilling system (e.g., the BHA 116 of FIG. 1B) if certain well trajectories were to be drilled. In this manner, an operator can select a particular well trajectory computed by the tool response simulator 320 showing predicted log data that the operator would like to achieve in actual measurements. Subsequently, during drilling operations to form or drill a selected well trajectory, the predicted log data can be compared to actual measurements collected using the downhole mud logging tool 138 of FIG. 1B or to the composition of the pumped fluid measured using the sampling while drilling tool 142 (FIGS. 1B-3B). The surface logging and control system 120 can use the results of these comparisons to control the directional drilling subsystem 118 (FIG. 1B) to adjust the trajectory of the well 102. In the illustrated example, the Petrel™ tool developed and sold by Schlumberger Technology Corporation can be used to implement the tool response simulator 320.

Figure 3B:
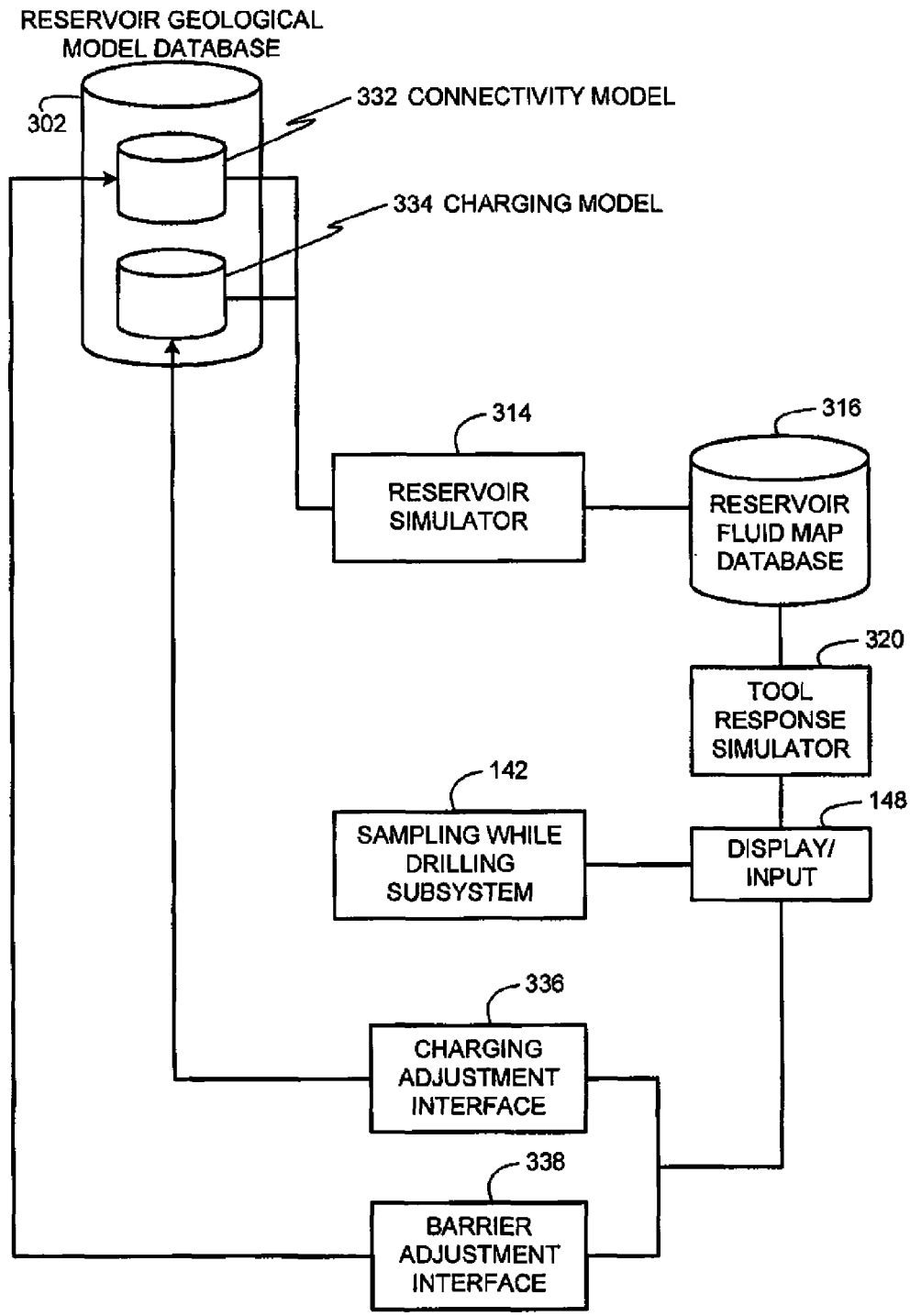
FIG. 3B depicts a portion of the example apparatus of FIG. 3A that can be used to detect and account for fluid compositional variations.

In the illustrated example, the example apparatus 300 is provided with or is coupled to the display/input interface unit 148 of FIGS. 1B, 3A, and 3B. The display/input interface unit 148 can be used to display to an operator the results of various operations based on the fluid map data, in conjunction with measurement data acquired by the BHA 116 and interpreted by the surface system 120. Based on the displayed information, the operator may elect to select a particular well trajectory via the display/input interface unit 148. The example apparatus 300 is provided with a trajectory adjustment interface 324 to store the user-selected well trajectory in the well trajectory database 306. In addition, the trajectory adjustment interface 324 can apply the operator's selection in real time by communicating commands to the BHA 116 to achieve the selected trajectory. For example, the trajectory adjustment interface 324 can communicate commands to the communications apparatus 128 of the BHA 116 to control the directional drilling subsystem 118 (FIGS. 1B and 3A) based on the selected well trajectory stored in the well trajectory database 306.

In the illustrated example, the BHA 116 is coupled to the example apparatus 300. In this manner, real-time measurements performed by the LWD tool 126 and/or the sampling while drilling tool 142 and/or the mud gas logging tool 138 can be used to update the formation evaluation logs database 304 and/or the fluid analysis reports database 308. In this manner, the data in the formation evaluation logs database 304 and/or the fluid analysis reports database 308 can subsequently be used to determine new fluid maps as the well is being drilled. In addition, real-time measurements performed by the MWD tool 124 can be used to update the current well trajectory data in the well trajectory database 306.

FIG. 3B illustrates a portion of the example apparatus 300 of FIG. 3A to show how the reservoir simulator 314 can, among other things, be used to detect fluid compositional variation in a reservoir. The detected variations may in turn be accounted for in the reservoir geological database 302 by inferring the occurrence of flow barriers (e.g., flow barrier 180 of FIG. 1B) or of reservoir charging (typically the history of an external flux of mass, such as gas or oil or even water in the reservoir). In the illustrated example, the reservoir simulator 314 simulates basin data. In some example implementations, the well 102 can be drilled along the reservoir R while monitoring the reservoir fluid properties to identify barriers to fluid flow. A barrier can be detected based on, for example but not exclusively, the detection of an abrupt change in the fluid pressure, the gas-oil ratio (GOR) or the color of the fluid within the reservoir R. Barrier detections can be confirmed using a vertical interference test or a drill stem test.

In the illustrated example, to detect fluid flows and barriers, the reservoir geological model database 302 stores connectivity model data 332 and charging model data 334. In other example implementations, the connectivity model data 332 and the charging model data 334 can be stored on a different database. The connectivity model data 332 describes faults, possible flow passages, flow resistance, etc. in the reservoir R. The charging model data 334 describes the source of downhole fluid (e.g., the composition, flow direction, etc.). In some example implementations, the connectivity model data 332 and the charging model data 334 may be represented as a function of geological time.

In the illustrated example, the reservoir simulator 314 uses the connectivity model data 332 and the charging model data 334 to predict the migration of the downhole fluids from one or more respective source rocks into other areas of the reservoir R and the change in the fluid composition(s) as a function of geological time. In addition, the reservoir simulator 314 can determine uncertainties for each of its predictions and store the predictions and their associated uncertainties corresponding to particular times (e.g., present time or future times) in the reservoir fluid map 316.

In operation, the data in the reservoir fluid map database 316 may be communicated to the tool response simulator 320, which uses the data to predict what the sampling while drilling tool 142 would measure if certain wellbore trajectories were followed. After following (e.g., drilling or forming) a particular wellbore trajectory, the sampling while drilling tool 142 (or the mud gas logging tool 138, not shown) performs actual formation fluid measurements, and a charging adjustment interface 336 and a barrier adjustment interface 338 can compare the actual measurements to the predicted data to determine whether to make adjustments to the charging model data 334 or the connectivity model data 332, respectively. For example, if the actual fluid sample measurements indicate inaccuracies in the connectivity model data 332, then the barrier adjustment interface 338 can adjust the connectivity model data 332 to better conform to the actual fluid sample measurements. By adjusting the connectivity model data 332 and the charging model data 334 based on actual fluid measurement analyses, the reservoir simulator 314 can determine relatively more accurate reservoir fluid map data for the reservoir fluid map database 316. In this manner, the connectivity model data 332 and/or the charging model data 334 can be adjusted until the predictions generated by the tool response simulator 320 and the actual fluid sample measurements are in substantial agreement. Thus, the presence of a barrier can be detected when the data predicted by the tool response simulator 320 is not in substantial agreement with the actual fluid sample measurements.

If the charging adjustment interface 336 and the barrier adjustment interface 338 determine that the actual fluid sample measurements are in substantial agreement (i.e., within the uncertainty of the measurement) with the predicted data generated by the tool response simulator 320, then the confidence about the reservoir fluid map data in the reservoir fluid map database 316 increases and, thus, the uncertainties associated with the reservoir fluid map data may be reduced in the reservoir fluid map database 316. Thus, the presence of a barrier can be confirmed when the data predicted by the tool response simulator 320 is in substantial agreement with the actual fluid sample measurements.

Figure 4A:
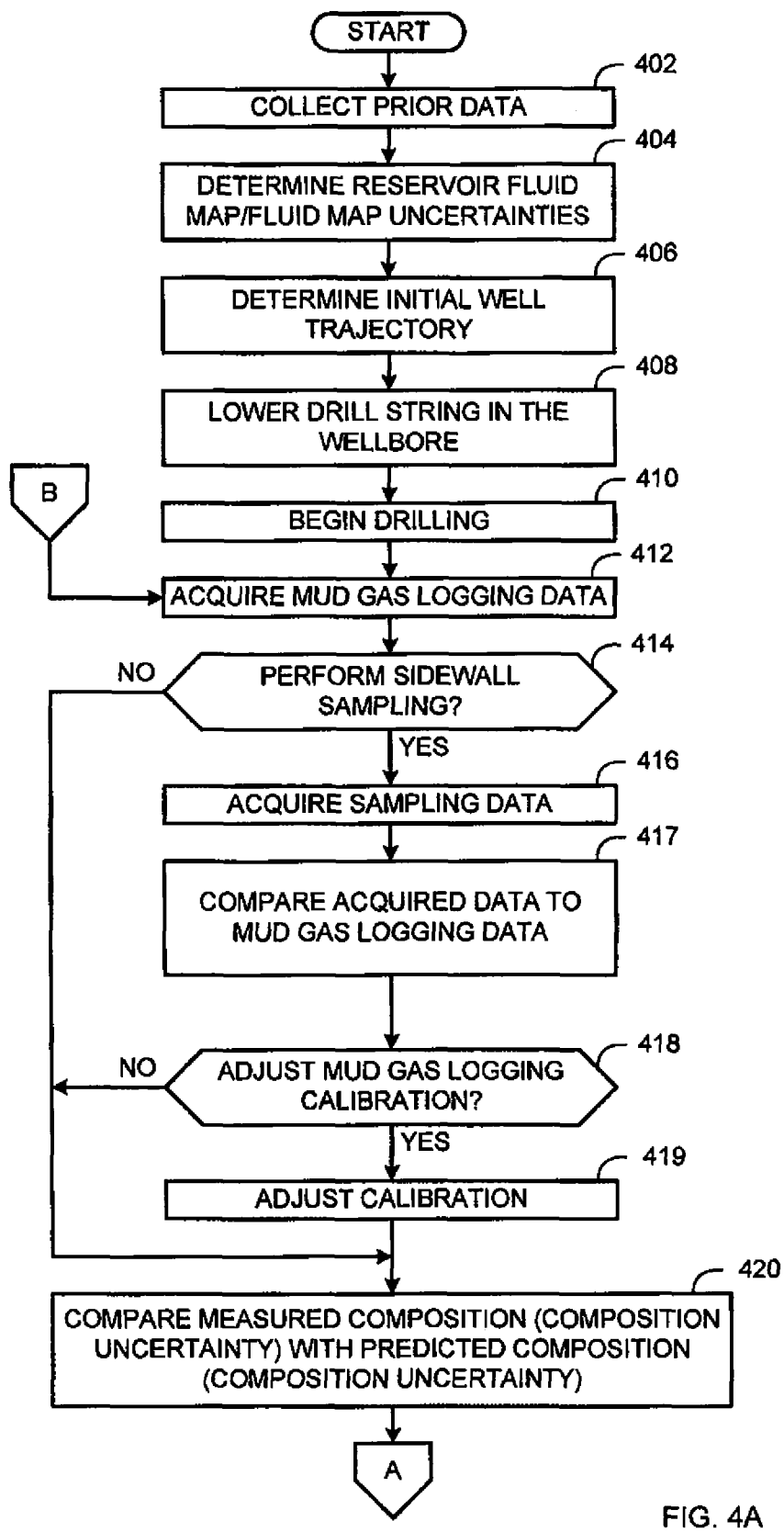
FIGS. 4A and 4B depict a flowchart of an example method that may be used to implement the example apparatus of FIG. 3 to control the well trajectory of a well.
Figure 4B:
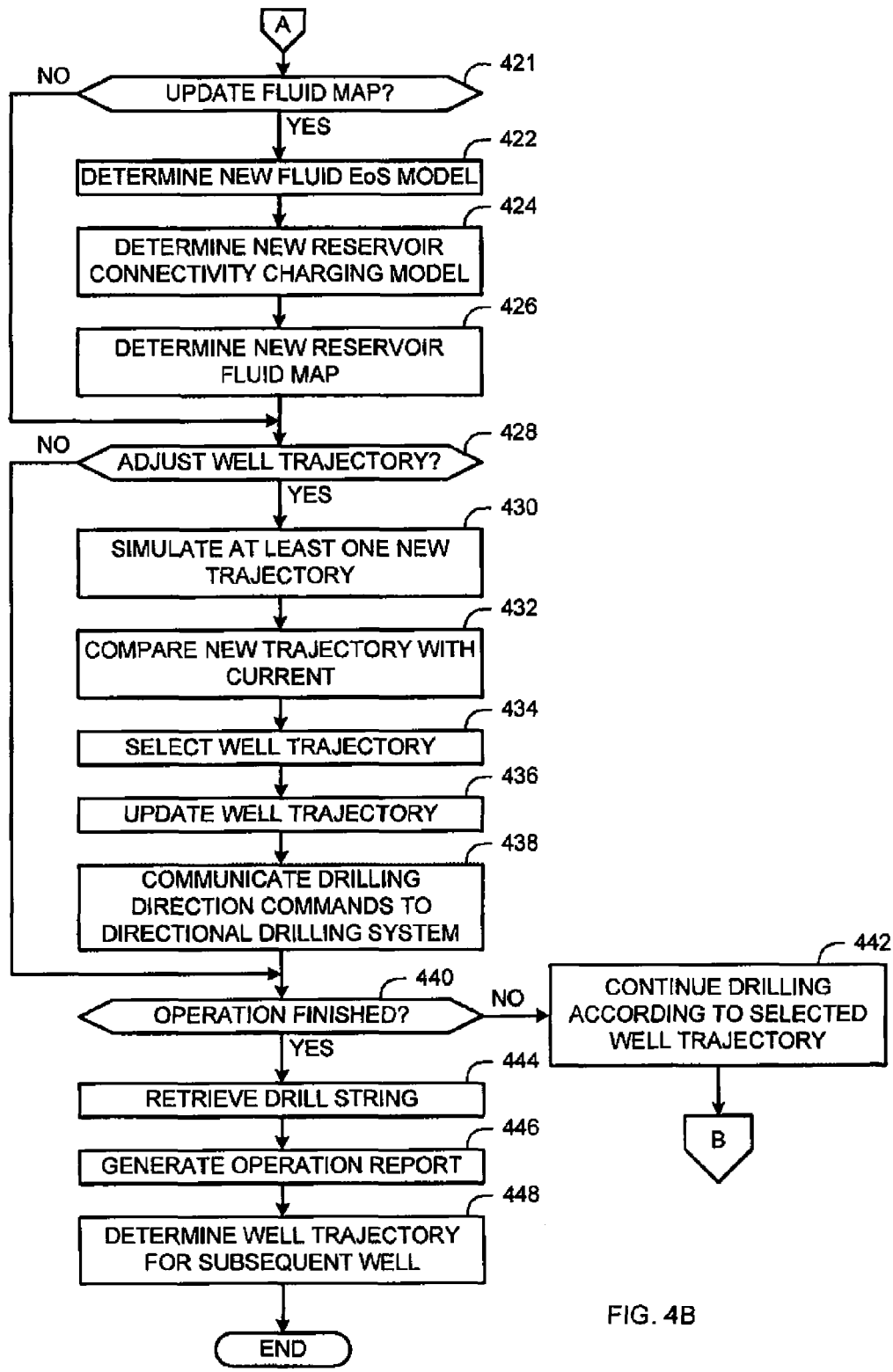

FIGS. 4A and 4B depict a flowchart of an example method that may be implemented with the example apparatus 300 of FIG. 3A to control the well trajectory of a well (e.g., the well 102 of FIG. 1B). The example method of FIGS. 4A and 4B may be implemented using software and/or hardware. Although the example method is described with reference to the flowchart of FIGS. 4A and 4B, other methods may additionally or alternatively be used. For example, the order of execution of the blocks depicted in the flowchart of FIGS. 4A and 4B may be changed, and/or some of the blocks described may be rearranged, eliminated, or combined.

Turning to FIG. 4A, initially, the example apparatus 300 collects prior data about the reservoir R in which the well 102 is to be drilled (block 402), if available. Prior data may include a seismic cube of the reservoir R, logs of previous wells drilled in the reservoir, laboratory results for fluid samples or core samples obtained from the reservoir, etc. In the illustrated example, the example apparatus 300 stores the prior data in the reservoir geological model database 302, the formation evaluation logs database 304, and the fluid analysis report database 308. If the prior data about the reservoir R is not available, measurements on a currently drilled well (e.g., the well 102 of FIG. 1B) can be performed to collect data about the reservoir R for the reservoir geological model database 302, the formation evaluation logs database 304, and/or the fluid analysis report database 308.

The reservoir simulator 314 (FIG. 3A) determines an initial reservoir fluid map from the prior data and determines an uncertainty map (block 404) of the reservoir R. The uncertainty map is used to indicate the uncertainties in the fluid property predictions in the well 102. The initial fluid map may have a high level of uncertainty. However, using the example methods and apparatus described herein in a recursive manner while drilling a well enables collecting data to reduce the uncertainties as the well is drilled and, thus, may update the well trajectory in real time based on updates to the fluid map as the uncertainties are reduced.

The well production simulator 318 or the tool response simulator 320 may be used by an operator to determine at least one initial well trajectory (block 406) based on, for example, the initial fluid map data determined at block 404 and stored in the reservoir fluid map database 316. In some example implementations, an initial well trajectory is designed to enable new fluid measurements to be made to reduce the uncertainty of the reservoir fluid map determined at block 404. In other example implementations, the well production simulator 318 is used to determine an initial well trajectory at block 406 that is designed to optimize hydrocarbon recovery from a reservoir. In yet other example implementations, the tool response simulator 320 can determine one or more well trajectories that are contingent on fluid measurements during the drilling of the well 102, and the tool response simulator 320 can be used to select one of the well trajectories at block 406 as the initial well trajectory to optimize a particular objective (e.g., particular fluid measurement data). The drill string 104 (FIG. 1B) is lowered in the well 102 (block 408), and drilling is started (block 410).

As described below, measurement data is collected by the BHA 116, and the measurement data can be used in real time by the example apparatus 300 of FIG. 3A to update reports, models, and simulations in the example apparatus 300. Measurement data can be collected before drilling, during drilling pauses, and/or after drilling the well 102 (e.g., while tripping out of the well).

In the illustrated example, the downhole mud gas logging tool 138 acquires downhole mud gas logging data (block 412). In other example implementations, surface mud gas logging data may be used instead of downhole mud gas logging data, but the surface mud gas logging data may not be accurately indicative of the actual characteristics of the subsurface reservoir R. Mud gas logging data can be acquired during drilling without the need to stop or pause drilling. In the illustrated example, the mud gas logging data is used to derive information about the formation F being drilled and, more particularly, about the most volatile components contained in the formation fluid which are entrained in the drilling fluid as the formation rock is crushed by the drill bit 106. The downhole mud gas logging tool 138 extracts these components from drilling mud in-situ and, more specifically, from drilling mud having formation fluid originating from within the formation F shortly after the drill bit 106 passes a given depth. In this manner, the downhole mud gas logging tool 138 can analyze the flashed gas composition in, for example, a continuous fashion. After accounting for the background composition (e.g., the composition of the incoming drilling fluid 26 (FIG. 1B) flowing from the drill bit 106), the change in the formation fluid composition introduced in the drilling fluid 26 by the drilling process may be determined.

In some example implementations, the mud gas logging tool 138 can monitor one or more molecular concentration(s) (e.g., methane concentration, ethane concentration, carbon dioxide concentration, concentration of a fluid injected in the reservoir etc. . . . ) extracted from the drilling mud samples after accounting for concentrations initially present in the drilling fluid 26 leaving the drill bit 106. In other example implementations, the mud gas logging tool 138 may also be used to monitor one or more concentration(s) of isotopes (e.g., the isotopes of carbon, 12C, 13C, etc. . . . ) associated with gases extracted from the drilling mud samples after accounting for concentrations initially present in the drilling fluid 26 leaving the drill bit 106. The monitored concentrations or other values derived therefrom are compared to corresponding log data predicted from the fluid map by the tool response simulator 320. In some cases, a discrepancy between measured data and predicted data greater than the measurement uncertainty may be indicative of compartmentalization that was not accounted for in the reservoir fluid model. In other cases, a discrepancy between measured data and predicted data greater than the measurement uncertainty may be indicative of the source of the methane, or carbon dioxide that was not accounted for in the reservoir fluid model. In yet other cases, a discrepancy between measured data and predicted data greater than the measurement uncertainty may be indicative of inaccurate composition gradients or inaccurate location of flood fronts in the fluid model.

In addition, the relative concentrations of the fluid constituents measured by the mud gas logging tool 138 may be used to distinguish between fluids in the reservoir and/or to indicate, but not necessarily prove, the origin of the fluids. For example, carbon isotope measurements can be used to advantage for identifying the origin and maturity of hydrocarbons. Less definitively, the commonly used mud-gas logging wetness and balance ratios, respectively, can be used to indicate the source of the gas occurring in the reservoir R. Other ratios, such as the Bernard ratio when plotted against the carbon isotope difference ratio, or plots of versus or versus the carbon isotope difference ratio can also be used as means for distinguishing between fluid origins.

In the illustrated example, the measurements made by the mud gas logging tool 138 may be used to determine if a sidewall fluid sampling operation should be performed (block 414). In the illustrated example, the surface system 120 uses the measurement information provided by the mud gas logging tool 138 and predicted information generated by the tool response simulator 320 to determine whether the fluid sampling operation should be performed. For example, a discrepancy between mud gas logging data measured by the mud gas logging tool 138 and predicted mud gas logging data generated by the tool response simulator 320 may be indicative of a flow barrier (e.g., flow barrier 180 of FIG. 1B) or a charging history improperly accounted for as the reservoir fluid map (stored in the reservoir fluid map database 316) has been determined. If such a discrepancy exists between the measured and the predicted mud gas logging data, a surface system 120 may cause the sampling while drilling tool 142 to extract and optionally to store one or more fluid samples from the formation and perform one or more fluid sample measurements. Thus, a sidewall fluid sampling operation may be performed if the mud gas logging data indicates that a significant change in fluid composition has occurred. Alternatively, a sidewall sampling operation may be scheduled at predetermined intervals or check points along the well trajectory such as, for example, close to expected gas-oil or oil-water contacts or other fluid transitions. In some example implementations, the operation of block 414 could be performed by an operator (e.g., an operator-performed decision) and the operator could provide user input based on the measurements made by the mud gas logging tool 138. For example, the computer 146 (FIG. 1B) could display the mud gas logging data received from the BHA 116 and the predicted mud gas logging data generated by the tool response simulator 320 via the terminal display/input console 148 using a display or presentation configuration or arrangement that facilitates an operator-performed comparison of the data.

If a sidewall sampling operation is to be performed (block 414), the sampling while drilling system 142 acquires sidewall sampling data (block 416). For example, the drilling operation of the BHA 116 is momentarily stopped and the probe 144 of the sampling while drilling tool 142 is extended to engage the formation F. The pump 202 is used to controllably draw fluid from the formation F. Fluid extraction continues until an acceptably low level of contamination (e.g., caused by seepage of the drilling fluid 26 into the formation F) in the sampled stream is obtained. One of the sensors 205 in the sampling while drilling tool 142 measures formation fluid pressure and temperature, and the spectrometer 204 measures fluid spectroscopic data of the fluid sample. A coarse fluid composition of the pristine formation fluid may be derived from the spectroscopic data, including partial concentrations such as methane concentration C1, ethane concentration C2, lumped concentration of propane, butanes and pentanes, C3-5, a lumped concentration of hydrocarbons having 6 or more carbon atoms in their molecules C6+, carbon dioxide concentration CO2. Also, GOR can be determined from the fluid composition, and asphaltene concentration may be derived from the optical density in the visible range measured using the spectrometer 204. In addition, water cut may be determined from spectroscopic data in the near infra-red range. Also, connate water acidity (pH), salinity (resistivity) can be determined. Finally, fluid mobility, fluid viscosity, and density may also be provided by analyzing the data obtained from one of the sensors 205.

The surface logging and control system 120 and/or the downhole electronics 208 compares the data derived from the measurements acquired during the sidewall sampling operation of block 416 with the mud gas logging data (acquired using the mud gas logging tool 138) (block 417). For example, the surface logging and control system 120 can compare fluid composition data such as fluid component concentrations, or any other measurement data acquired during the sidewall sampling operation or data derived from the measurement data, such as uncertainty levels.

The surface logging and control system 120 then determines whether it should adjust a calibration of the mud gas logging tool 138 (block 418). For example, the surface logging and control system 120 can determine that it should adjust the mud gas logging calibration if the comparison between the sidewall sampling measurement and the mud gas logging data performed at block 417 indicates that the mud gas logging data is not sufficiently in agreement with the sidewall sampling measurement within an acceptable measurement uncertainty. For example, the results of the mud gas logging tool 138 can be recalibrated based on the sidewall sampling measurements to provide an updated or relatively more accurate set of continuous fluid property logs along the well trajectory. In some example implementations, to compare the mud gas logging data to the sidewall sampling measurements, the surface logging and control system 120 compares a subset of fluid composition components (e.g., C1-C8) acquired using the mud gas logging tool 138 to the same component concentrations measured during the sidewall sampling operation. Alternatively, the surface logging control system 120 can compare ratios of hydrocarbon concentrations acquired using the mud gas logging tool 138 to ratios of the same hydrocarbon concentrations acquired using the sidewall sampling operation.

If the surface logging and control system 120 determines that it should adjust the mud gas logging calibration (block 418), the surface logging and control system 120 adjusts the mud gas logging calibration (block 419). In the illustrated example, the surface logging and control system 120 can adjust the mud gas logging calibration by updating fluid component ratios used as the calibration data. For example, if the calibration data includes a methane concentration calibration parameter and the mud gas logging measurement data indicates a methane concentration ratio of 60% while the sidewall sampling measurement indicates a methane concentration ratio of 50%, the calibration parameter corresponding to the methane concentration ratio can be adjusted until the mud gas logging measurement data indicates a methane concentration ratio of 50% in agreement with the sidewall sampling measurement. Calibration data for other fluid components measured using the mud gas logging tool 138 can be adjusted in a similar manner. The surface logging and control system 120 can store the mud gas logging calibration data in a memory in the mud gas logging tool 138 for subsequent use by the mud gas logging tool 138.

After the surface logging and control system 120 adjusts the mud gas logging calibration (block 419) or if the surface logging and control system 120 determines that it should not adjust the mud gas logging calibration data (block 418) or if a sidewall sample measurement is not performed (block 414), the surface logging and control system 120 compares at least one of the measured fluid composition data (and its composition uncertainty) derived from the measurements acquired by the mud gas logging tool 138 at block 412 and the measured fluid composition data (and its composition uncertainty) derived from the measurements acquired during the sidewall sampling operation of block 416 with the predicted and/or desired (or target) composition data (and its composition uncertainty) (block 420). For example, the surface logging and control system 120 can compare fluid composition data, temperature, pressure, fluid component concentrations, or any other measurement data acquired or data derived from the measurement data. Measured composition data or other properties derived therefrom can be compared to a log predicted by the tool response simulator 320 (FIG. 3A) based on the reservoir fluid map data in the reservoir fluid map database 316.

In some example implementations, the comparison operation of block 420 could be performed by an operator (e.g., an operator-performed comparison) and the operator could provide user input based on the comparison (e.g., a decision to update the reservoir fluid map in the reservoir fluid map database 316 based on the comparison, etc.). For example, the computer 146 (FIG. 1B) could receive from the BHA 116 the measured fluid composition data derived from the measurements acquired by the mud gas logging tool 138 at block 412 and/or from the measurements acquired during the sidewall sampling operation of block 416. The computer 146 could further display the received measured fluid composition data and a log predicted from the reservoir fluid map data via the terminal display/input console 148 using a presentation configuration or arrangement that facilitates an operator-performed comparison of the data.

The surface logging and control system 120 determines whether to update the reservoir fluid map in the reservoir fluid map database 316 (block 421) (FIG. 4B). For example, the surface logging and control system 120 may determine whether to update the reservoir fluid map based on the comparisons between fluid composition measurements and prediction composition data performed at block 420. In the illustrated example, the surface logging and control system 120 can determine that it should update the reservoir fluid map when a discrepancy is observed between the sidewall sampling data and the measurement data predicted from the fluid map (e.g., a gas-oil contact is incorrectly located on the fluid map) and/or the mud gas logging data and the predicted measurement data. Whether discrepancies exist to warrant an update to the reservoir fluid map may be based on whether differences between the compared data indicate discrepancies that exceed an acceptable discrepancy threshold. The value or level of the discrepancy threshold may be directly related to the amount or magnitude of uncertainty in the measured and/or predicted composition data such that if the uncertainty is relatively large, the discrepancy threshold may be set to be more accepting of larger differences, whereas if the uncertainty is relatively small, the discrepancy threshold may be set to be less accepting of larger differences. When no discrepancies warranting an update of the fluid map are detected based on the comparisons, the surface logging and control system 120 can elect not to update the reservoir fluid map. In instances in which an initial reservoir fluid map is not available, the surface logging and control system 120 may determine at block 421 to generate a reservoir fluid map when a sufficient amount of data has been collected by the BHA 116.

If the surface logging and control system 120 determines that it should update the reservoir fluid map data, corrections can be made to the reservoir fluid map stored in the reservoir fluid map database 316. In the illustrated example, the fluid simulator 312 (FIG. 3A) determines a new fluid EoS model using the downhole fluid composition analysis data generated by the mud gas logging tool 138 and/or the downhole fluid composition analysis data generated by the sidewall sampling tool 142 (block 422). Example methods that can be used to determine the new fluid EoS model are described in U.S. Patent Application Publ. No. 2007/0119244, which is hereby incorporated herein by reference in its entirety.

Significant differences between the measured composition of the fluid and the fluid composition indicated by the fluid map (determined for example at block 420) can be indicative of erroneous predicted data (e.g., a horizontal composition gradient has been omitted from the data used to determine the predicted measurements) and/or one or more conditions in a reservoir. In the illustrated example of FIGS. 4A and 4B, the differences may be indicative of an inaccurate charging model (e.g., the charging model data 334 of FIG. 3B) for the reservoir R and, thus, the charging adjustment interface 336 determines a charging model for the reservoir R (block 424) by, for example, fitting a methane or carbon dioxide charging model to the measurements collected by the mud gas logging tool 138. Additionally or alternatively, the differences may be indicative of an inaccurate temperature charging model in the reservoir R, and the charging adjustment interface 336 can fit a new temperature model to the temperature data points collected by the sampling while drilling tool 142 along the drilled well trajectory.

Another reason for the differences may be that an inaccurate fluid connectivity model 332 was used for determining the reservoir fluid map of the reservoir R stored in the reservoir fluid map database 316. The inaccuracy may be detected from pH measurements in contiguous aquifers, or observed deviations of hydrocarbon compositions from composition gradients predicted using thermodynamic equilibrium (or an appropriate flux model if thermodynamic equilibrium is not indicated). In case such an inaccuracy is detected, the barrier adjustment interface 338 can update the geological model data in the reservoir geological model database 302 to reflect possible barriers to flow that cannot be detected with petrophysical logs, geologic logs, or seismic surveys. The fluid connectivity model 332 may be iteratively altered or adjusted until the differences between the measured composition of the fluid and the fluid composition indicated by the fluid map are within the uncertainty of the measurements. The iterative adjustment may require modifying seal or fault positions or transmissibilities, which may be inferred from pressure data, LWD data such as resistivity imaging data, acoustic imaging data, pressure testing data and the like.

When the measured data matches the predicted data along the well 102, the reservoir simulator 314 determines a new reservoir fluid map (block 426) by populating the fluid composition properties measured at the well over the reservoir R and the fluid composition uncertainty map in the reservoir fluid map database 316. In some cases, it may be found that ambiguities or discrepancies in the reservoir architecture need to be resolved to obtain a reservoir fluid map.

The example apparatus 300 then determines whether it should adjust the well trajectory (block 428). For example, if the updated reservoir fluid map in the reservoir fluid map database 316 is significantly different from the reservoir fluid map used to plan the well, if an ambiguity or anomaly is detected in the reservoir architecture, or if a measured fluid property differs substantially from its predicted value, an operator may elect to adjust the well trajectory, as further described in connection with FIGS. 5, 6, 7, 8, and 9.

If an adjustment to the well trajectory is considered to be warranted (block 428), the new well trajectory may be determined by simulating one or more new well trajectory(ies) (block 430) and comparing the merit of one or more new well trajectory(ies) (block 432) to the current well trajectory in the well trajectory database 306. For example, the display/input interface 148 can display the one or more new well trajectories in association with a current well trajectory to enable an operator to select one of the new well trajectories. The operations of blocks 430 and 432 may be repeated in an iterative fashion by iteratively simulating new well trajectories and comparing each to the current well trajectory until one of the new simulated well trajectories is selected (block 434) by, for example, an operator. In some example implementations, the well production simulator 318 (FIG. 3A) is used to implement the operations of blocks 430, 432, and 434 to select a well trajectory to optimize the reservoir drainage/production to, for example, produce the most economical value. For example, the well production simulator 318 can simulate the drainage/production corresponding to various well trajectories, and an operator can select the trajectory leading to the most economical value. Alternatively, the tool response simulator 320 (FIG. 3A) can be used to simulate wells based on predicted fluid properties (e.g., fluid composition), and a well trajectory can be selected by, for example, an operator based on a desired (or target) measured fluid property corresponding to the predicted fluid properties. The desired (or target) measured fluid properties may be associated with steering the well to follow fluid transition features or to avoid or stay away from other features (e.g., fluid contacts or tar mats).

After a well trajectory is selected (block 434), the display/input interface 148 (FIGS. 1B, 3A, and 3B) updates the well trajectory in the well trajectory database 306 (block 436), and the surface logging and control system 120 (FIG. 1B) communicates drilling direction commands to the directional drilling system 118 (FIGS. 1B and 3A) (block 438) to adjust the trajectory of the well 102 (FIG. 1B).

The example apparatus 300 then determines whether the drilling operation is finished (block 440). For example, the drilling operation may be finished if the well 102 is completed and drilling has reached a desired (or target) goal or objective (e.g., a desired drainage/production). Alternatively, the drilling operations may be finished if it is determined that no trajectory simulated by the well production simulator 318 or the tool response simulator 320 (FIG. 3A) achieves a desired goal, in which case drilling operations can be halted on a currently drilled well and another well may be started to try and achieve the desired goal.

If drilling operations have not finished (block 440), the BHA 116 continues drilling according to the selected well trajectory (block 442) stored in the well trajectory database 306, and control returns to block 412 of FIG. 4A. However, if drilling operations have finished (block 440), the surface logging and control system 120 instructs the platform and derrick assembly 100 to retrieve the drill string 104 (block 444) and, thus, the BHA 116. The surface logging and control system 120 and/or the computer 146 can generate an operation report (block 446) and determine a well trajectory for a subsequent well (block 448). The example process of FIGS. 4A and 4B is then ended.

Although the example method of FIGS. 4A and 4B is described as being performed in real time while the BHA 116 is in the well and the well 102 is being drilled, in other example implementations, the example method can be performed in near real time. That is, the data collected during the drilling of the well 102 can be analyzed once the BHA 116 is brought to surface. In such example implementations, a reservoir fluid map can be created and/or updated as part of an operation report after the well 102 has been drilled. The operation report may also include laboratory analysis data of the samples drawn while drilling and a comparison of the laboratory analysis data and the real time in-situ measurement data. In some example implementations, the trajectory of the next well to be drilled in the reservoir R can be determined based on the reservoir fluid map as described above in connection with blocks 402, 404, and 406 of FIG. 4A.

Although not shown, other reservoir information may also be updated while performing the example method of FIGS. 4A and 4B to, for example, generate the operation report at block 446. For example, the updated data can include a reservoir fluid pressure map, a geology/lithology map, and a structural (fault, flow barriers) map. To update this data, other LWD deep measurements (e.g., deep azimuthal resistivity measurements, acoustic imaging measurements, formation testing while drilling measurements, etc.) could be performed by the BHA 116 and the results may be used to update the maps.

FIGS. 5, 6, 7, 8, and 9 are flowcharts of example methods that may be used to adjust well trajectories to achieve particular desired (or target) results associated with well drainage/ production and/or to avoid or target particular structural features in a reservoir. The example methods of FIGS. 5, 6, 7, 8, and 9 may be implemented in combination with FIGS. 4A and 4B. For example, the example methods of FIGS. 5, 6, 7, 8, and 9 may be implemented as variations of the example method of FIGS. 4A and 4B to implement respective processes. The example methods of FIGS. 5, 6, 7, 8, and 9 may be implemented using software and/or hardware. Although the example methods are described with reference to the flowcharts of FIGS. 5, 6, 7, 8, and 9, the order of execution of the blocks depicted in the flowchart of FIGS. 5, 6, 7, 8, and 9 may be changed, and/or some of the blocks described may be rearranged, eliminated, or combined to achieve the same or similar results.

Figure 5:
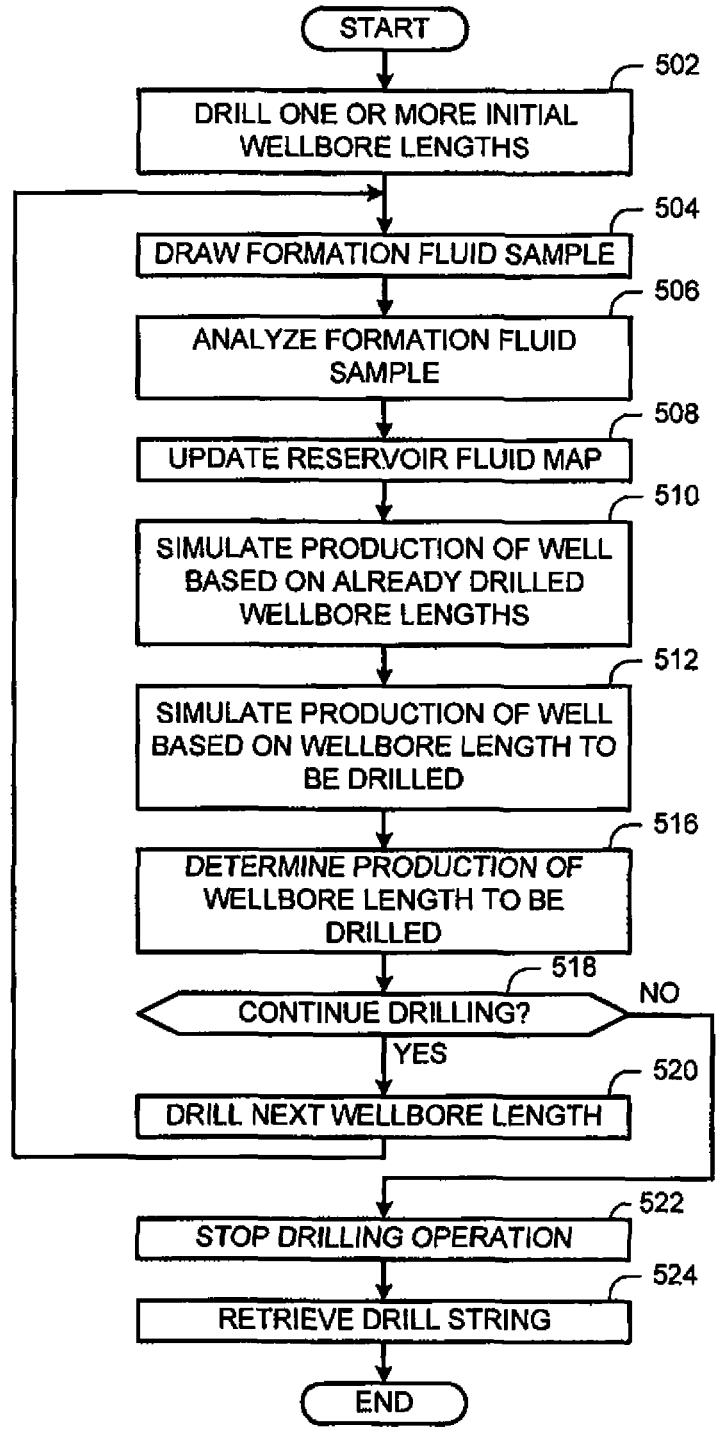
FIG. 5 is a flowchart of an example method that may be used to determine whether to stop drilling operations based on real-time well production simulations.

Turning to FIG. 5, an example method to determine whether to stop drilling operations based on real-time well production simulations involves predicting or estimating the production that can be achieved from an additional wellbore length yet to be drilled in a well (e.g., the well 102 of FIG. 1B). At some point during a drilling process the estimated production data for a subsequent wellbore length to be drilled may indicate a lower economical value (e.g., a low production, a production incompatible with the planned surface facility, etc.) than the cost of drilling the additional length. Thus, the drilling process can be stopped.

As shown in FIG. 5, initially one or more initial wellbore length(s) are drilled (block 502). The sampling while drilling tool 142 (FIGS. 1B-3B) draws a formation fluid sample (block 504) and analyzes the fluid sample (block 506). For example, the sampling while drilling tool 142 can draw the formation fluid sample via the probe 144 and analyze the fluid sample using the spectrometer 204 and/or the one or more additional sensor(s) 205 (FIG. 2). Alternatively, the mud gas logging tool 138 is used to capture a portion of the formation fluid present in the drilling fluid 126 once the formation rock has been crushed (block 504) and analyses a flashed portion of the formation fluid (block 506). Preferably, but not necessarily, the sampling while drilling tool 142 and/or the mud gas logging tool 138 measures one or more of formation mobility, GOR, fluid composition, density, viscosity, pressure, and temperature.

The reservoir simulator 314 updates the reservoir fluid map data stored in the reservoir fluid map database 316 of FIG. 3A (block 508). In some example implementations, the reservoir simulator 314 adjusts the biodegradation gradient simulated for the reservoir R to match the fluid sample measurements. In other example implementations, the reservoir simulator 314 adjusts the thermal gradient simulated for the reservoir R to match the fluid sample measurement. In yet other example implementations, the fluid sample measurements acquired by the sampling while drilling tool 142 or the mud gas logging tool 138 may indicate that the BHA 116 has entered or is entering a new compartment in the reservoir R containing a different fluid and, thus, the reservoir simulator 314 adjusts the reservoir fluid map data in the database 316 accordingly.

The well production simulator 318 (FIG. 3A) simulates the production of the well based on the already drilled wellbore lengths (block 510). In the illustrated example, the well production simulator 318 simulates the production of the well based on the one or more wellbore lengths drilled at block 502. The well production simulator 318 also simulates the production of the well 102 based on the wellbore length to be drilled (block 512). That is, the well production simulator 318 simulates the production of the well 102 based on the one or more wellbore lengths drilled at block 502 in combination with the wellbore length to be drilled. In some instances, the well production simulator 318 may simulate production at block 512 based on a plurality of possible wellbore lengths that may be drilled, each having a different trajectory to determine which trajectory of which length will have the most production. In this manner, the well production simulator 318 may select the most promising wellbore length and trajectory with which to proceed to the operation of block 516.

The well production simulator 318 then determines the production of the wellbore length to be drilled (block 516). In some instances, the well production simulator 318 may determine that the production from the added wellbore length to be drilled is small due to, for example, the formation fluid being too viscous, the pressure being too low for the well to be economically produced, the formation F being of a poorer quality than had been anticipated, and/or elements in the fluid will rapidly precipitate and clog the part of the formation where the well 102 is to be drilled. Additionally or alternatively, the well production simulator 318 may determine that the production from the added length will result in producing too much gas at the surface and that the production facilities which have to be constructed to handle the produced gas would be prohibitively costly.

The surface logging and control system 120 then determines whether to continue drilling (block 518) the additional wellbore length. For example, the display/input interface 148 (FIGS. 1B, 3A and 3B) can receive input from an operator indicating whether to continue or stop drilling operations. If the surface logging and control system 120 determines that drilling should continue (block 518), the surface logging and control system 120 instructs the BHA 116 to drill the next wellbore length, and control is passed back to the operation of block 504. Otherwise, the surface logging and control system 120 instructs the BHA 116 (FIG. 1B) to stop drilling operations (block 522), and the platform and derrick assembly 100 retrieves the drill string 104 (block 524). The example process of FIG. 5 is then ended. In some example implementations, the well 120 may be drilled further if, for example, other productive portions of the reservoir R may be reached by continuing to drill the well 120 even if the immediately subsequent length to be drilled is predicted to be uneconomical to produce.

Figure 6:
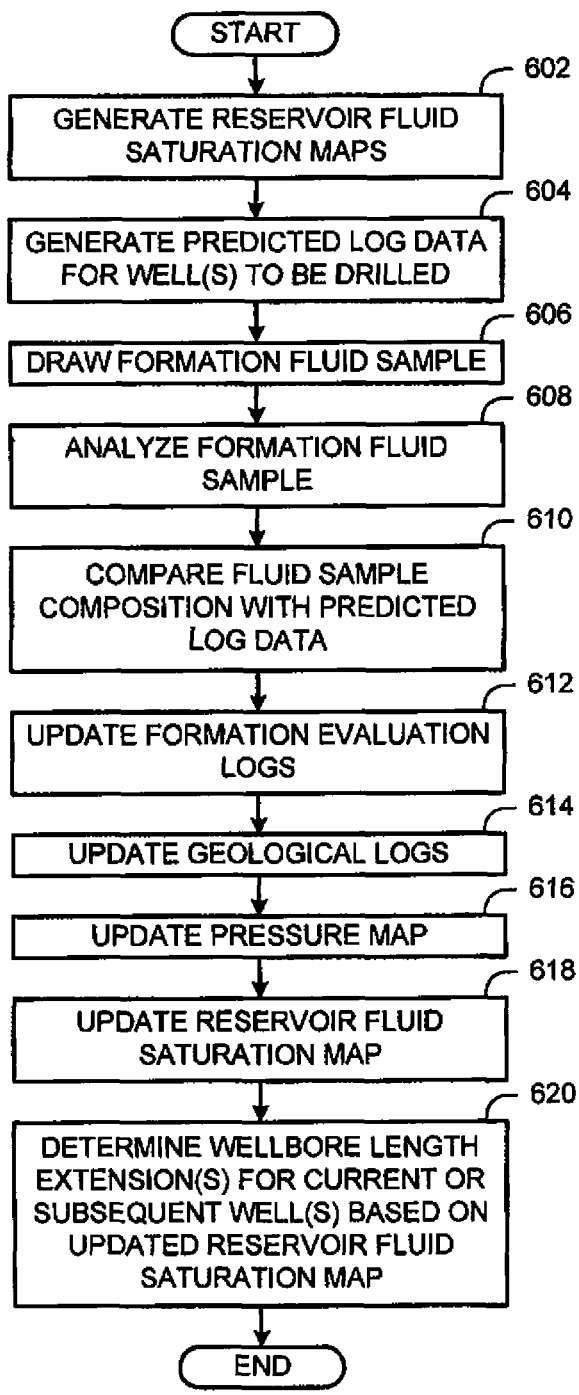
FIG. 6 is a flowchart of an example method that may be used to place a well in a reservoir containing injected fluid.

Turning to FIG. 6, the depicted example method can be used to place a well in a reservoir containing injected fluid, such as gas. The example method may be used, for example, in instances in which new wells are drilled with the intent of recovering bypassed oil in a reservoir that has been under primary production or has been produced using injection. In the illustrated example, the example method is implemented to follow primary production by injecting gas which is miscible with the oil remaining in the reservoir R with the expectation that the oil recovery factor will increase. However, two typical concerns associated with the management of gas injection schemes include maintaining the gas pressure above a minimum miscibility pressure and knowing the position of the injection front throughout the reservoir R. Using the depicted example method of FIG. 6, the uncertainty in knowing the location of the injected gas front can be progressively reduced as new wells are drilled, thus improving the placement of current, sidetrack or future wells. To further reduce the uncertainty in knowing the location of the injected gas front, the pressure in the reservoir R may be monitored at various locations along newly drilled wells.

As shown in FIG. 6, initially, the reservoir simulator 314 may generate a reservoir fluid saturation map, that is representative of, amongst other things, the distribution of relative proportions of pristine formation fluid and/or injection fluid in the reservoir R (e.g., a saturation level of injected fluid) (block 602). In the illustrated example, the reservoir simulator 314 may generate at least a gas saturation map and additionally a pressure contour map, both of which reflect the incremental gas injection history and the oil production at the producing wells. The tool response simulator 320 generates predicted fluid measurement log data for one or more well(s) to be drilled (block 604). Some of the predicted log data may correspond to anticipated fluid sampling log data based on the fluid saturation map generated at block 602 at stations where in-situ fluid compositions are to be sampled. Other predicted log data may include a pressure profile along a well having pressures acquired at the same sampling station. Yet other predicted log data may correspond to possible gas breakthrough from a nearby injection well.

The sampling while drilling tool 142 (FIGS. 1B-3B) draws a formation fluid sample (block 606) and analyzes the fluid sample (block 608). For example, the sampling while drilling tool 142 can draw the formation fluid sample via the probe 144 and analyze the fluid sample using the spectrometer 204 and/or the one or more additional sensor(s) 205 to determine a fluid sample composition, and in particular the relative proportions of pristine formation fluid and/or injection fluid in the fluid sample. Alternatively, the mud gas logging tool 138 may be used to analyze the composition formation fluid (e.g., analyze a concentration ratio between methane, or any other injected gas such as carbone dioxide, and another group of hydrocarbons such as embodied in the so called wetness ratio commonly used in mud gas logging). Preferably, but not necessarily, the measurements performed by the sampling while drilling tool 142 and/or the mud gas logging tool 138 include mass spectra measurements, gas chromatography measurements, optical reflectance measurements, optical absorbance spectra measurements in the near infra red range (e.g., at wavelengths characteristic of oil, methane and carbon dioxide), emulsion detection measurements from ultraviolet fluorescence, pressure measurements, temperature and fluid density measurements, and/or viscosity and mobility measurements.

A fluid sample composition determined at block 608 is then compared to the predicted and/or desired (or target) (e.g., sufficiently low) log data determined at block 604 (block 610). In the illustrated example, the comparison is used along with pressure measurements for a proposed well to determine if the pressure in the proposed well is sufficient for an injected gas to be miscible with in-situ oil and if the gas injection scheme is effective in contacting and mobilizing the remaining oil in the well formation F (FIG. 1B). When the comparison of block 610 is performed for different points along the proposed well, each comparison may indicate a different result such that some portions of the proposed well have sufficient pressure while others may not. In the illustrated example, the comparison of block 610 will also indicate what changes should be made to reservoir fluid map data in the reservoir fluid map database 316 to reflect the latest data acquired at block 608.

For each one of the well(s) to be drilled, the reservoir simulator 314 updates respective formation evaluation logs in the formation evaluation logs database 304 (block 612) and geological logs in the reservoir geological model database 302 (block 614). In the illustrated example, the example apparatus 300 also updates the pressure map in the reservoir fluid map database 316 (block 616) and the reservoir fluid saturation map in the reservoir fluid map database 316 (block 618). The updates of blocks 612, 614, 616, and 618 facilitate determining a more accurate reservoir fluid saturation map and associated uncertainty map of the reservoir R. In example implementations in which the comparison of block 610 indicates no change in the formation evaluation model and the geological model, the formation evaluation model and the geological model need not be updated at block 612 and 614.

The example apparatus 300 determines one or more possible wellbore length extension(s) that can be drilled in a current or one or more subsequent well(s) based on the updated reservoir fluid saturation map (block 620). For example, additional possible lengths may include lengths that steer the well 102 (FIG. 1B) in a different direction or that continue drilling in the same direction to acquire additional information to make subsequent drilling decisions. For example, the additional information may be used to better understand the injection gas front of the reservoir R (FIG. 1B) to plan a next well in the reservoir R. In the illustrated example, the example apparatus 300 (or an operator using the apparatus 300) may determine based on the comparison of block 610 that no subsequent lengths should be drilled and that the drilling of a current well should stop when, for example, the well in its current form may be used as a producer or as a gas injector.

In some example implementations, the operations of block 610 and/or 620 could be performed by an operator (e.g., a database update decision based on the comparison, a well trajectory selection based on the comparison, etc.) and the operator could provide user input to the example apparatus 300, based on a display or presentation configuration or arrangement that facilitates an operator-performed comparison of the data via the terminal display/input console 148.

Figure 7:
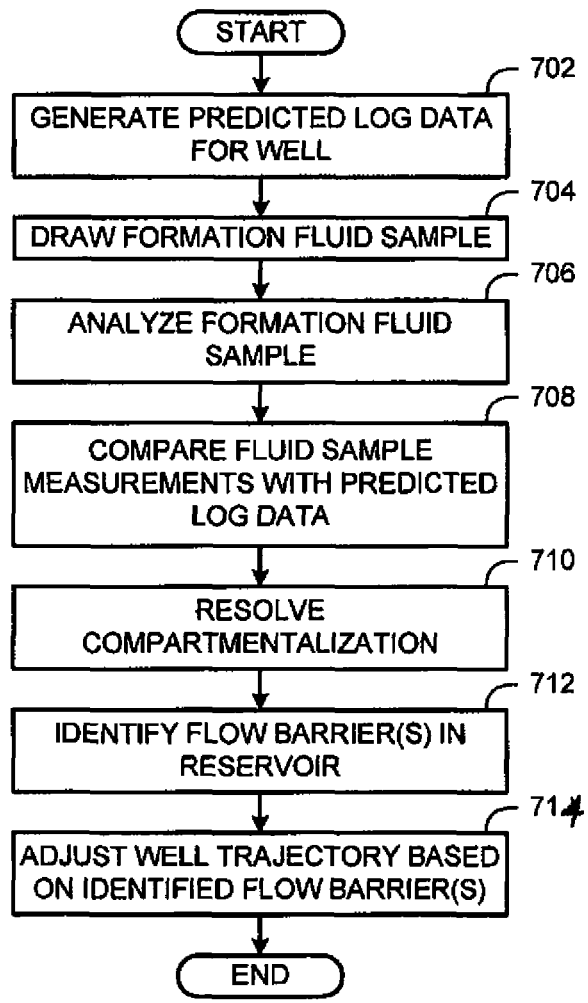
FIG. 7 is a flowchart of an example method that may be used to adjust well trajectories to plan a well in a compartmentalized reservoir.

Turning to FIG. 7, the depicted example method can be used to adjust well trajectories to plan a well in a compartmentalized reservoir. In the illustrated example of FIG. 7, potential compartmentalization in a reservoir is resolved during the drilling of the well, and the well trajectory can be modified based on an understanding of the fluid heterogeneity in the compartmentalized reservoir. Barriers to fluid flow in a compartmentalized reservoir are typically properties of the geological structures that contain the fluids. Barriers to fluid flow in rock structures often manifest themselves in measurable changes in fluid properties; for example, as a discontinuous change in some fluid parameter (e.g., parameters that can be measured using downhole fluid analysis (DFA) techniques include, a color parameter, a GOR parameter, an asphaltene content parameter, a $CO_2$ content parameter, a gas composition parameter, a density parameter, a viscosity parameter, a pH parameter and a salinity parameter). In addition, flow barriers often manifest themselves by having higher density fluid in the oil column at locations which would violate static equilibrium. In the illustrated example described below, predicted data from a current geologic model is used to find flow barriers (e.g., flow barrier 180 of FIG. 1B). In addition, the example method of FIG. 7 can be used to detect barriers or possible barriers based on measurement data acquired using other tools such as, for example, the PeriScope™ resistivity tool developed and sold by Schlumberger Technology Corporation. The example method of FIG. 7 can be implemented using several DFA stations, each positioned on a different side of a potential barrier to detect fluid manifestations of barriers.

As shown in FIG. 7, initially the tool response simulator 320 generates predicted fluid measurement log data for a well (block 702). In the illustrated example, the predicted log data corresponds to fluid composition and/or fluid properties such as, for example, mass density and viscosity, typically in a sand shale sequence along a first trajectory. The sampling while drilling tool 142 (FIGS. 1B-3B) draws a formation fluid sample (block 704) and analyzes the fluid sample (block 706). For example, the sampling while drilling tool 142 can draw the formation fluid sample via the probe 144 and analyze the fluid sample using the spectrometer 204 and/or the one or more additional sensor(s) 205. Preferably, but not necessarily, the measurements acquired using the sampling while drilling tool 142 include fluid density and viscosity measurements, mass spectra measurements, gas chromatography measurements, and/or optical absorbance spectra measurements. At block 706 the sampling while drilling tool 142 and/or the surface logging and control system 120 (FIG. 1B) can use the mass spectra, gas chromatography, and/or optical absorbance spectra measurements to determine, at least, the proportions of C1, C2, C3-5, C6+, $CO_2$, $H_2O$, and, in the case of optical absorbance, color, which can be used to determine the GOR and various ratios of combinations of the hydrocarbon components in the fluid sample.

The fluid sample measurements (and/or fluid composition) determined at block 706 are compared to the predicted log data determined at block 702 (block 708). In addition, fluid compartmentalization is resolved (block 710) and the existence and locations of flow barriers (e.g., flow barrier 180 of FIG. 1B) in the reservoir are identified (block 712) based on the fluid compartmentalization. The operations of blocks 708, 710, and 712 can be performed by an operator observing the different data and/or comparisons thereof via the display/input interface 148 (FIGS. 1B, 3A, and 3B). In other example implementations, the operations of blocks 708, 710, and 712 can be implemented using software and/or hardware configured to perform such analyses.

The example apparatus 300 then adjusts the well trajectory (block 710) based on flow barriers identified at block 712 (block 714). For example, if a fluid composition or fluid property falls outside the predicted range determined at block 702, a well trajectory may be adjusted to intersect a separate sand shale sequence to check the fluid contained therein. In some example implementations, different well trajectories contingent on fluid findings can be developed prior to beginning drilling operations of a well. The example process of FIG. 7 is then ended. Although not shown, the process of FIG. 7 can be repeated until a well is completely drilled or until a determination is made that drilling operations should no longer continue for the well.

In some example implementations using the example method of FIG. 7, other thermodynamic models based on first principles can be used to model the variations in concentration of asphaltenes and resins in a fluid. Asphaltenes and resins are the heaviest components of crude oil. Hydrocarbons could have minimal concentration variations of relatively lighter components and yet have an identifiable concentration variation of asphaltenes and or resins. Asphaltenes and resins dictate or influence the color of crude oil and can be measured in-situ by DFA techniques. Preferably, but not necessarily, under sampling conditions in which a fluid is pristine and no phase transitions have occurred, DFA measurement techniques can be used to achieve relatively more accurate measurement data of asphaltene-resin concentrations in a fluid. Variations in asphaltene and resin concentrations can be indicators of reservoir compartments. The large molecular aggregates of asphaltenes and resins are subject to buoyancy forces and, thus, anomalous changes in the natural distribution of these components within reservoirs are typically indicative of flow barriers.

Figure 8:
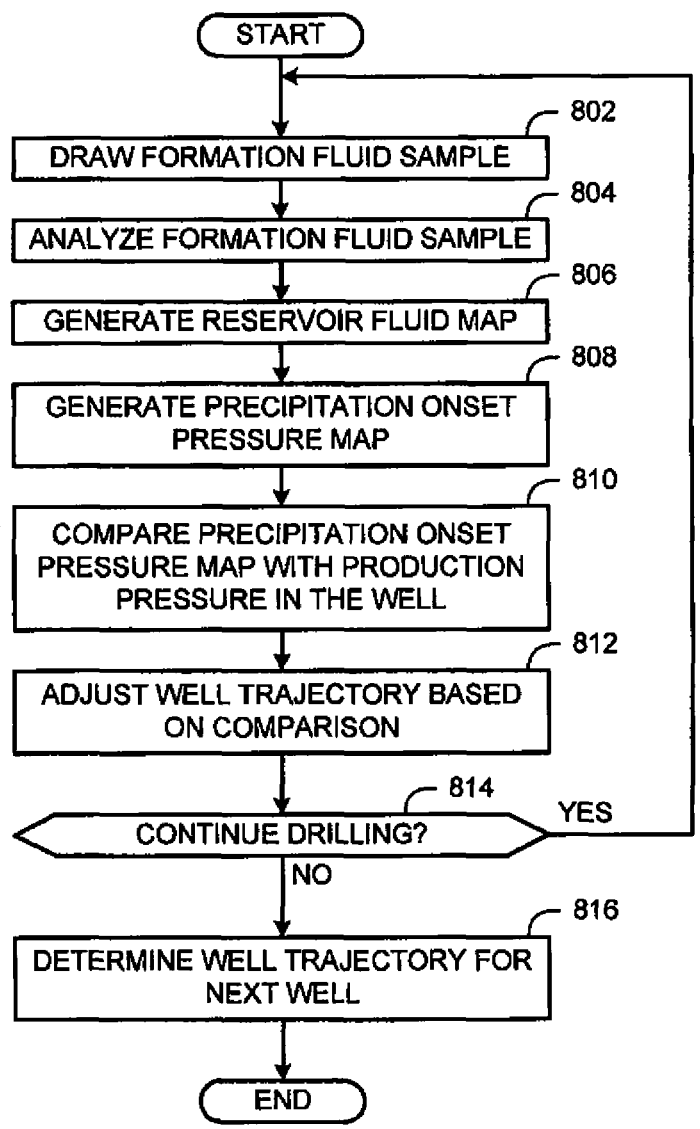
FIG. 8 is a flowchart of an example method that may be used to steer a well trajectory based on asphaltene precipitation onset pressure.

Turning to FIG. 8, the depicted example method can be used to steer a well based on asphaltene precipitation onset pressure. In the illustrated example, the example method can be used to produce wells having relatively fewer flow assurance problems than might be achieved using other, traditional drilling techniques. The example method of FIG. 8 uses characteristics such as, for example, fluid compositions represented by a reservoir fluid map to generate an asphaltene precipitation onset pressure map. In this manner, a well trajectory can be steered based on the precipitation onset pressure map.

As shown in FIG. 8, initially, the sampling while drilling tool 142 (FIGS. 1B-3B) draws a formation fluid sample (block 802) and analyzes the fluid sample (block 804). For example, the sampling while drilling tool 142 can draw the formation fluid sample via the probe 144 and analyze the fluid sample using the spectrometer 204 and/or the one or more additional sensor(s) 205. Preferably, but not necessarily, the measurements acquired using the sampling while drilling tool 142 include measures of optical absorption in the visible range and pressure measurements. Asphaltene typically causes an optical absorption that varies in the visible light range exponentially with the light frequency. Typically, asphaltene concentrations can be determined when gravity segregation and chemical equilibrium in the reservoir R are acting to generate or influence the presence of such asphaltene concentrations. At block 804, the sampling while drilling tool 142 and/or the surface logging and control system 120 (FIG. 1B) correlate the color of the formation fluid to an asphaltene concentration in the fluid to refine the asphaltene concentration measure based on the formation fluid color.

The reservoir simulator 314 then generates a reservoir fluid map (block 806) based on the asphaltene concentration. The reservoir fluid map can be determined by modeling how gravity segregation and chemical equilibrium affects variations in the concentrations of asphaltene at different subsurface depths. The fluid simulator 312 (FIG. 3A) generates a precipitation onset pressure map (block 808) based on the reservoir fluid map generated at block 806. In the illustrated example, the fluid simulator 312 generates the precipitation onset pressure map using an EoS equation.

The example apparatus 300 (or an operator) then compares the precipitation onset pressure map with production pressure in the well (block 810). For example, the precipitation onset pressure map generated at block 808 can be compared to production pressures predicted by the well production simulator 318 and pressure measurements acquired at block 804. In some example implementations, the comparison operation of block 810 could be performed by an operator (e.g., an operator-performed comparison) and the operator could provide user input based on the comparison (e.g., a well trajectory selection based on the comparison, etc.). For example, the computer 146 (FIG. 1B) could receive the precipitation onset pressure map from the fluid simulator 312 and production pressures from the well production simulator 318 and display the at least a portion of precipitation onset pressure map and production pressures via the terminal display/input console 148 using a display or presentation configuration or arrangement that facilitates an operator-performed comparison of the data.

The example apparatus 300 then adjusts the well trajectory based on the comparison (block 812). For example, the direction of drilling may be adjusted to avoid zones in the reservoir R that have a precipitation pressure that is too low. Thus, the well trajectory adjustment of block 812 may be made based on the comparison at block 810 and a comparison of measured and predicted fluid properties that are computed from a fluid composition (e.g., precipitation onset pressure, equation of state (EoS), etc.).

For example, if a measured fluid composition indicates a precipitation onset pressure that is significantly different from a desired (or target) value, the well trajectory may be adjusted at block 812 to avoid zones in the reservoir R that have a precipitation pressure that is too low and/or to achieve a well trajectory that will produce a desired (or target) fluid precipitation pressure along the drilled well. In some cases, drilling of a well may be stopped when it is determined that subsequent drilling will not achieve a desired (or target) or necessary precipitation pressure.

The example apparatus 300 then determines whether the BHA 116 (FIG. 1B) should continue drilling a current well (block 814). For example, the example apparatus 300 may determine based on the comparison of block 810 that the drilling of the current well should be stopped if subsequent drilling will not achieve a desired or necessary precipitation pressure. Otherwise, if a well trajectory is selected at block 812 that can avoid zones in the reservoir R that have a precipitation pressure that is too low, drilling may continue. If drilling is to continue, control is passed back to block 802. Otherwise, control passes to block 816, and the example apparatus 300 is used to determine a well trajectory for a next well (block 816). In the illustrated example, a well trajectory for a side track well to be drilled in the same reservoir R may be determined based on the precipitation onset pressure map. The example process of FIG. 8 is then ended.

Figure 9:
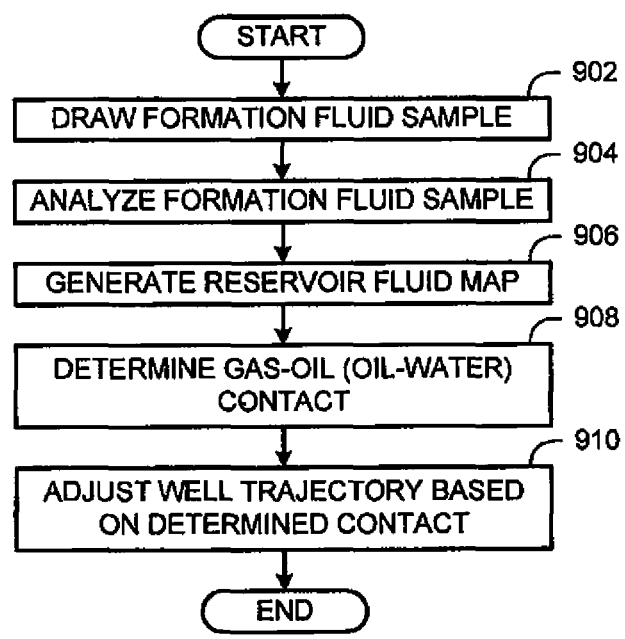
FIG. 9 is a flowchart of an example method that may be used to control the trajectory of a well to maintain the well trajectory below a gas-oil contact in an oil zone.

Turning to FIG. 9, the depicted example method can be used to control the trajectory of a well (e.g., an almost horizontal well) to maintain the well trajectory below a gas-oil contact in an oil zone. The example method of FIG. 9 can be advantageously used to determine relatively better well trajectories relative to gas-oil contacts than can be achieved using resistivity tools because gas-oil contacts do not offer a resistivity contrast. Also, in the case of light hydrocarbons having a transition to rich condensate gas, little or relatively low acoustical contrast between the oil zone and the gas zone exists. However, the example method of FIG. 9 can be advantageously used to determine relatively better well trajectories relative to gas-oil contacts than can be achieved using acoustic tools. Where relatively large gradients in fluid properties exist, the example method of FIG. 9 can be advantageously used to determine the gas-oil contact and adjust a well trajectory based on that gas-oil contact.

As shown in FIG. 9, initially, the sampling while drilling tool 142 (FIGS. 1B-3B) draws a formation fluid sample (block 902) and analyzes the fluid sample (block 904). For example, the sampling while drilling tool 142 can draw the formation fluid sample via the probe 144 and analyze the fluid sample using the spectrometer 204 and/or the one or more additional sensor(s) 205. Preferably, but not necessarily, the measurements acquired using the sampling while drilling tool 142 include GOR, C1, C2, C3-C5, and C6+ concentrations, and saturation pressure, i.e. bubble point/dew point pressure, measurements at reservoir temperature. Alternatively or additionally the mud gas logging tool 138 may be used to acquire composition data of the reservoir fluid.

The reservoir simulator 314 then generates a reservoir fluid map (block 906) based on the measurements acquired at block 904, including fluid composition and/or saturation pressure predictions. In the illustrated example, to generate the reservoir fluid map, the fluid simulator 312 assumes that a chemical equilibrium exists in the reservoir R. The fluid simulator 312 also determines or identifies the existence of a gas-oil (or water-oil) contact in the fluid map generated at block 906 (block 908).

The example apparatus 300 then adjusts a well trajectory based on the determined contact (block 910). For example, the example apparatus 300 may adjust the well trajectory to maintain the well in an oil zone at a desired (or target) distance from the gas-oil contact determined at block 908. The well trajectory may be adjusted at block 910 based on the contact identified at block 908 by comparing a measured fluid property (e.g., a fluid composition and/or a saturation pressure) and a fluid property predicted in the fluid map. The point of the fluid map at which the measured and predicted properties match indicates a distance from a gas-oil contact. If the indicated distance is significantly different from a desired (or target) distance, the well trajectory may be adjusted to achieve a desired distance. The example process of FIG. 9 is then ended. Although not shown, the process of FIG. 9 can be repeated until a well is completely drilled or until a determination is made that drilling operations should no longer continue for the well.

In some example implementations, the comparison operation of block 910 could be performed by an operator (e.g., an operator-performed comparison) and the operator could provide user input based on the comparison (e.g., a well trajectory selection based on the comparison). For example, the computer 146 (FIG. 1B) could receive fluid properties (e.g., a fluid composition and/or a saturation pressure) measured along the well trajectory from the BHA 116 and display the received fluid properties on the reservoir fluid map via the terminal display/input console 148 using a presentation configuration or arrangement that facilitates an operator-performed comparison of the BHA 116 location and gas-oil contact location.

In some example implementations, the example methods of FIG. 9 can also be used to adjust or steer well trajectories relative to an oil-water contact or to maintain a position relative to biomarkers or the quality of an oil body where the quality is, for example, a measure of the degree of biodegradation that has taken place. In such example implementations, measurements acquired using the sampling while drilling tool 142 at block 904 include measurements of benzene and toluene in the case of the oil-water contacts, fluid composition measurements up to at least C30 in the case of biodegradation, and/or carbon and hydrogen isotopic ratio measurements. To determine fluid compositions based on biodegradation, the sampling while drilling tool 142 can alternatively be used to measure in-situ density, GOR, gas gravity, and viscosity, and the degree of biodegradation may be inferred from local correlations of such measurements.

In view of all of the above and the figures, those skilled in the art should readily recognize that the present disclosure introduces a method comprising acquiring mud gas logging data, comparing the mud gas logging data to second data associated with a sidewall fluid sample measurement, and adjusting calibration data associated with a mud gas logging tool based on the comparison of the mud gas logging data and the second data associated with the sidewall fluid sample measurement. The method may further comprise performing the comparison of the mud gas logging data to the second data when the mud gas logging data indicates a change in a fluid composition. The second data may be one of a fluid composition or a concentration of a fluid component.

The present disclosure also introduces a method comprising acquiring mud gas logging data, comparing the mud gas logging data to one of a predetermined fluid composition or a predetermined concentration of a fluid component, and initiating a sidewall fluid sample measurement based on the comparison. Such method may further comprise acquiring second data associated with a sidewall fluid sample measurement. Such method may further comprise comparing the mud gas logging data to the second data, and adjusting calibration data associated with a mud gas logging tool based on the comparison of the mud gas logging data and the second data.

The present disclosure also introduces an apparatus comprising a mud gas logging tool configured to acquire mud gas logging data and comprising a first sensor operatively coupled to a tool inlet for admitting fluid contained in a well. The apparatus further comprises a sidewall fluid sampling tool operatively coupled to the mud gas logging tool and comprising a second sensor configured to selectively couple to a formation penetrated by the well to acquire sidewall fluid sample measurements. The apparatus may further comprise a directional drilling assembly configured to adjust a well trajectory based on at least one of mud gas logging data and sidewall fluid sample measurements. The apparatus may further comprise a probe configured to form a fluid communication with the formation penetrated by the well.

The present disclosure also introduces a method comprising determining a reservoir fluid property map on a portion of a reservoir, conveying a fluid property sensor into a reservoir well, using the sensor to perform in-situ measurements indicative of a formation fluid property, comparing the in-situ measurements with the property map, and adjust a well trajectory based on the comparison. Such method may further comprising determining a reservoir fluid property uncertainty map on at least the same portion of the reservoir, determining the uncertainty associated with the in-situ measurements performed by the sensor, and comparing the in-situ measurement uncertainties with at least one of the property map and its associated uncertainty map. Conveying the fluid property sensor into the reservoir well may use at least one of a drill string and a wireline.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method, comprising:
   directing a mixture comprising first formation fluid and drilling mud from a wellbore annulus into a mud gas logging tool;
   acquiring mud gas logging data by analyzing the mixture to determine first fluid type estimations;
   directing second formation fluid through a sidewall of the wellbore and into a sampling tool;
   acquiring second data associated with a sidewall fluid sample measurement by analyzing the second formation fluid;
   comparing the mud gas logging data to the second data associated with the sidewall fluid sample measurement to determine whether the first fluid type estimations are as expected; and
   adjusting calibration data associated with the mud gas logging tool in response to determining that the first fluid type estimations are not as expected.

2. The method of claim 1 further comprising performing the comparison of the mud gas logging data to the second data in response to determining that the mud gas logging data indicates a change in a fluid composition.

3. The method of claim 1 wherein the second data is one of a fluid composition or a concentration of a fluid component.

4. The method of claim 1, wherein analyzing comprises measuring a composition of gases separated from the mixture.

5. The method of claim 1, wherein the sampling tool is coupled to the mud gas logging tool as part of a bottom hole assembly.

6. The method of claim 1, wherein analyzing the second formation fluid comprises performing optical spectrometer measurements.

7. The method of claim 1, wherein directing second formation fluid comprises extending a probe from the sidewall of the sampling tool to engage a wall of the wellbore.

8. A method, comprising:
   directing a first mixture from an annulus of a wellbore into a mud gas logging tool;
   acquiring first mud gas logging data by analyzing the first mixture to determine first fluid type estimations;
   generating predicted fluid type estimations using the acquired first mud gas logging data;
   directing a second mixture from the annulus into a mud gas logging tool;
   acquiring second mud gas logging data by analyzing the second mixture to determine second fluid type estimations;
   determining whether the second fluid type estimations correspond to the predicted fluid type estimations; and
   initiating a sidewall fluid sample measurement through a sidewall of the wellbore in response to determining that the second fluid type estimations do not correspond to the predicted fluid type estimations.

9. The method of claim 8 further comprising acquiring second data associated with the sidewall fluid sample measurement.

10. The method of claim 9 further comprising:
comparing the second mud gas logging data to the second data associated with the sidewall fluid sample measurement; and
adjusting calibration data associated with a mud gas logging tool based on the comparison of the second mud gas logging data and the second data associated with the sidewall fluid sample measurement.

11. The method of claim 8, wherein the predicted fluid type estimations comprise a predetermined fluid composition.

12. The method of claim 8, wherein the predicted fluid type estimations comprise a predetermined concentration of a fluid component.

13. The method of claim 8, wherein initiating a sidewall fluid sample measurement comprises directing formation fluid into a sidewall of a downhole tool.

14. The method of claim 8, wherein initiating a sidewall fluid sample measurement comprises extending a probe from a sidewall of a downhole tool to engage a formation and directing fluid from the formation into the downhole tool through the probe.

15. An system, comprising:
a mud gas logging tool configured to acquire mud gas logging data and comprising a first sensor operatively coupled to a tool inlet for admitting fluid contained in a well;
a sidewall fluid sampling tool operatively coupled to the mud gas logging tool and comprising a second sensor configured to selectively couple to a formation penetrated by the well to acquire sidewall fluid sample measurements;
a controller configured to determine first fluid type estimations based on the acquired mud gas logging data, to employ the acquired sidewall fluid sample measurements to determine whether the first fluid type estimations correspond to expected fluid type estimations, and to adjust calibration data associated with the mud gas logging tool in response to determining that the first fluid type estimations do not correspond to the expected fluid type estimations.

16. The apparatus of claim 15 further comprising a directional drilling assembly configured to adjust a well trajectory based on at least one of mud gas logging data and sidewall fluid sample measurements.

17. The apparatus of claim 15 further comprising a probe configured to form a fluid communication with the formation penetrated by the well.

* * * * *